(12) United States Patent
Zhao et al.

(10) Patent No.: US 12,383,426 B2
(45) Date of Patent: Aug. 12, 2025

(54) MEDICAL PENETRATION DEVICE AND SYSTEM

(71) Applicant: Beijing Sightnovo Medical Technology Co., Ltd, Beijing (CN)

(72) Inventors: Chan Zhao, Beijing (CN); Chaoran Xia, Beijing (CN); Yueguang Sun, Beijing (CN); Chuan Li, Beijing (CN)

(73) Assignee: BEIJING SIGHTNOVO MEDICAL TECHNOLOGY CO., LTD, Beijing (CN)

( * ) Notice: Subject to any disclaimer, the term of this patent is extended or adjusted under 35 U.S.C. 154(b) by 0 days.

(21) Appl. No.: 18/285,476

(22) PCT Filed: May 12, 2022

(86) PCT No.: PCT/CN2022/092561
§ 371 (c)(1),
(2) Date: Oct. 3, 2023

(87) PCT Pub. No.: WO2022/237885
PCT Pub. Date: Nov. 17, 2022

(65) Prior Publication Data
US 2024/0180745 A1    Jun. 6, 2024

(30) Foreign Application Priority Data

May 13, 2021 (WO) ............... PCT/CN2021/093646

(51) Int. Cl.
*A61F 9/00* (2006.01)
*A61M 5/24* (2006.01)
*A61M 5/32* (2006.01)

(52) U.S. Cl.
CPC ......... *A61F 9/0008* (2013.01); *A61M 5/2448* (2013.01); *A61M 5/2466* (2013.01); *A61M 5/3202* (2013.01); *A61M 2005/2474* (2013.01)

(58) Field of Classification Search
CPC ...... A61M 5/178; A61M 5/17; A61M 5/3129; A61M 5/2455; A61M 5/2466;
(Continued)

(56) References Cited

U.S. PATENT DOCUMENTS 2,866,458 A * 12/1958 Hein, Jr. ............. A61M 5/2033
604/138
5,167,641 A    12/1992 Schmitz
(Continued)

FOREIGN PATENT DOCUMENTS

CN    103037802 A    4/2013
CN    103284832 A    9/2013
(Continued)

OTHER PUBLICATIONS

International Preliminary Report on Patentability, issued Nov. 14, 2023, for PCT Application No. PCT/CN2021/093646, filed May 13, 2021, 8 pages.
(Continued)

*Primary Examiner* — Laura A Bouchelle
(74) *Attorney, Agent, or Firm* — MORRISON & FOERSTER LLP

(57) ABSTRACT

A medical puncturing device and a system comprising medical apparatuses configured to be assembled into the medical puncturing device. The device or system comprises: a syringe barrel (1) comprising a distal closed end and a proximal open end; an elastic movement unit comprising an actuation member (2) and a floating seal (3) inside the syringe barrel (1), where the actuation member (2) and a floating seal (3) are capable of forming an elastic connection such that the actuation member (2) and floating seal (3) are capable of moving forward and backward relative to one another; a hollow puncture needle (6) fixedly connected to the actuation member (2) and proximal to the floating seal
(Continued)

(3), where the hollow puncture needle (6) comprises a needle distal opening (6a) and a needle body opening (6b); and a flowable composition lumen (7) enclosed by the syringe barrel distal closed end, an inner wall of the syringe barrel, and the floating seal (3). The device or system is configured to advance the hollow puncture needle (6) distally. Prior to use, the needle distal opening (6a) can be proximal to the floating seal (3), within the floating seal (3), between the floating seal (3) and a distal seal (8) at the syringe barrel distal closed end, within the distal seal (8), or distal to the distal seal (8). The hollow puncture needle (6) is advanced through the floating seal (3) and the syringe barrel distal closed end, thereby connecting the flowable composition lumen (7), the needle body opening (6b), and the needle distal opening (6a). The present disclosure enables injection, access, expansion, and/or device implantation in an apparent or potential tissue void, cavity, or vessel, and is especially useful for achieving precise control of puncturing depth and needle placement, as well as steady injection and injection of a defined volume.

17 Claims, 20 Drawing Sheets

(58) Field of Classification Search
CPC ............ A61M 2005/3101; A61M 2005/3103; A61M 2005/312; A61M 2005/3117; A61M 2005/3118; A61F 9/0008
See application file for complete search history.

(56) References Cited

U.S. PATENT DOCUMENTS

| | | | |
|---|---|---|---|
| 5,620,421 | A | 4/1997 | Schmitz |
| 7,331,984 | B2 | 2/2008 | Tu et al. |
| 9,180,047 | B2 | 11/2015 | Andino |
| 9,539,139 | B2 | 1/2017 | Andino |
| 9,572,800 | B2 | 2/2017 | Zarnitsyn |
| 9,636,253 | B1 | 5/2017 | Andino |
| 9,636,332 | B2 | 5/2017 | Zarnitsyn |
| 9,770,361 | B2 | 9/2017 | Andino |
| 9,937,075 | B2 | 4/2018 | Andino |
| 10,517,756 | B2 | 12/2019 | Andino |
| 10,555,833 | B2 | 2/2020 | Andino |
| 2009/0209903 | A1 | 8/2009 | Cherif-Cheikh et al. |
| 2015/0005689 | A1 | 1/2015 | Horvath |
| 2015/0011926 | A1 | 1/2015 | Reitsamer |
| 2016/0151204 | A1 | 6/2016 | Haffner |
| 2016/0175535 | A1 | 6/2016 | Becker |
| 2019/0274882 | A1 | 9/2019 | Romoda |
| 2020/0069883 | A1 | 3/2020 | Karp |
| 2021/0045772 | A1 | 2/2021 | Pinchuk |
| 2024/0358547 | A1 | 10/2024 | Zhao |

FOREIGN PATENT DOCUMENTS

| | | | |
|---|---|---|---|
| CN | 210749813 | U | 6/2020 |
| CN | 112603646 | A | 4/2021 |
| CN | 215273198 | U | 12/2021 |
| CN | 215307335 | U | 12/2021 |
| CN | 215349326 | U | 12/2021 |
| CN | 215349934 | U | 12/2021 |
| JP | H10-305097 | A | 11/1998 |
| WO | 2007087061 | A2 | 8/2007 |
| WO | 2007100745 | A2 | 9/2007 |
| WO | 2015196085 | A2 | 12/2015 |
| WO | 2016042162 | A1 | 3/2016 |
| WO | 2016196841 | A1 | 12/2016 |
| WO | 2017210627 | A1 | 12/2017 |
| WO | 2018083619 | A1 | 5/2018 |
| WO | 2021/079189 | A1 | 4/2021 |
| WO | 2022236779 | A1 | 11/2022 |
| WO | 2022237887 | A1 | 11/2022 |

OTHER PUBLICATIONS

International Preliminary Report on Patentability, issued Nov. 14, 2023, for PCT Application No. PCT/CN2021/093650, filed May 13, 2021, 7 pages.
International Preliminary Report on Patentability, issued Nov. 14, 2023, for PCT Application No. PCT/CN2022/092561, filed May 12, 2022, 9 pages.
International Preliminary Report on Patentability, issued Nov. 14, 2023, for PCT Application No. PCT/CN2022/092563, filed May 12, 2022, 9 pages.
International Search Report and Written Opinion, mailed Aug. 17, 2022, for PCT Application No. PCT/CN2022/092561, filed May 12, 2022, 14 pages.
International Search Report and Written Opinion, mailed Aug. 18, 2022, for PCT Application No. PCT/CN2022/092563, filed May 12, 2022, 15 pages.
International Search Report and Written Opinion, mailed Feb. 10, 2022, for PCT Application No. PCT/CN2021/093646, filed May 13, 2021, 13 pages.
International Search Report and Written Opinion, mailed Feb. 10, 2022, for PCT Application No. PCT/CN2021/093650, filed May 13, 2021, 13 pages.

* cited by examiner

MEDICAL PENETRATION DEVICE AND SYSTEM

CROSS-REFERENCE TO RELATED APPLICATION

This application is a national stage application under 35 U.S.C. § 371 of International Application No. PCT/CN2022/092561, filed internationally on May 12, 2022, which claims priority to International Patent Application No. PCT/CN2021/093646, filed May 13, 2021, entitled "Medical Penetration Device and System," which are herein incorporated by reference in their entireties for all purposes.

FIELD

The present disclosure in some aspects relates to the field of medical device and apparatus, and specifically a device, kit, assembly, or system for medical penetration.

BACKGROUND

In existing methods of treatment involving the suprachoroidal space (SCS), a regular syringe is typically used to inject a medication into the SCS. When performing the puncture, the punctuation depth of a needle of the syringe needs to be manually controlled, and a medical personnel has to rely on his or her experience to determine if the needle has entered the SCS. However, the eye structure of different patients usually vary from each other and the determination of needle depth by the medical personnel may not be accurate. As a result, the precise placement of the needle relative to the SCS cannot be guaranteed. Furthermore, when injecting the medication, the plunger of the syringe has to be constantly pressed manually. Skillful operation by the medical personnel is required in order to stabilize the injection speed and prevent fluctuations in the flow speed. However, in practice, it is challenging to guarantee steady injection every time. Improved devices and methods for medical penetration such as injection into the SCS are needed. The present disclosure addressed these and other needs.

SUMMARY

To address at least one of the defects or shortcomings in existing devices and methods, the present disclosure in some aspects provides a kind of medical puncturing device and a medical kit, assembly, or system for medical penetration, which can achieve injection, access, expansion, and/or device implantation in the suprachoroidal space or other apparent or potential tissue gaps, cavity or cavity systems, and vessels. The present disclosure is especially useful for achieving precise control of puncturing depth and needle placement, as well as steady injection and injection of a defined volume.

The present disclosure in some aspects provides a medical puncturing device (e.g., an injector) enabling precise needle placement in a tissue, a system comprising the medical puncturing device, a kit comprising components to assemble the medical puncturing device, and a medical apparatus assembly comprising one or more of the components.

In some embodiments, provided herein is a system comprising a syringe barrel comprising a proximal end and a distal end; a floating seal in the syringe barrel; a needle base proximal to the floating seal (e.g., the needle base is closer to an operator while the floating seal is closer to a subject), and the floating seal and the needle base are configured to elastically engage each other. In some embodiments, the system further comprises a needle comprising a needle proximal end and a needle distal end, and the needle proximal end engages the needle base. In any of the embodiments herein, the needle proximal end can be fixed to the needle base or releasably attached to (e.g., inserted in) the needle base. In any of the embodiments herein, the needle can comprise: (i) a needle distal opening, (ii) a needle body opening between the needle proximal end and the needle distal end, and (iii) a needle body passageway connecting the needle distal opening and the needle body opening. In any of the embodiments herein, the needle body opening can be proximal to the needle distal opening. In any of the embodiments herein, the needle base can be configured to advance the needle distally toward the floating seal (e.g., when the needle distal end is proximal to the floating seal) and/or through the floating seal (e.g., when the needle distal end has entered or pierced into the floating seal).

In any of the embodiments herein, a proximal lumen and a distal lumen can be provided in the syringe barrel on different sides of the floating seal. In any of the embodiments herein, the floating seal can separate the proximal lumen and the distal lumen. The proximal and distal lumens can be enclosed by the same syringe barrel or by different syringe barrels that belong to separate syringe units that can be assembled together. In any of the embodiments herein, the distal lumen can comprise a flowable composition, such as a liquid, a solution, a suspension, a gel, an oil, an ointment, an emulsion, a cream, a foam, a lotion, a paste, or any combination or mixture thereof.

In any of the embodiments herein, prior to advancement of the needle, the needle body opening and the needle distal opening can be proximal to the floating seal. In any of the embodiments herein, the needle body opening and the needle distal opening can be in the proximal lumen. In any of the embodiments herein, the needle base can be configured to advance the needle distally toward the floating seal. For example, the needle can be advanced through the proximal lumen. In any of the embodiments herein, the needle base can be configured to advance the needle further distally through the floating seal. In any of the embodiments herein, the needle body opening can be in the proximal lumen while the needle distal opening is in the distal lumen. In any of the embodiments herein, advancement of the needle through the floating seal can comprise puncturing the floating seal with the needle distal end. In any of the embodiments herein, the floating seal can comprise a guiding groove that aligns with the needle to facilitate the puncturing. In any of the embodiments herein, advancement of the needle through the floating seal can comprise advancing the needle distal end through an existing aperture or slit in the floating seal.

In any of the embodiments herein, the needle base can be configured to advance the needle distally such that both the needle body opening and the needle distal opening are distal to the floating seal. In any of the embodiments herein, the needle body opening and the needle distal opening can be in the distal lumen, e.g., contacting the flowable composition. In any of the embodiments herein, the needle base can be configured to advance the needle distally through the distal lumen such that the needle body opening is in the distal lumen while the needle distal opening is outside the distal lumen. In any of the embodiments herein, when the needle distal opening is outside the distal lumen, the needle distal opening can contact a distal seal (e.g., distal seal 8) of the syringe barrel. In any of the embodiments herein, when the needle distal opening is outside the distal lumen, the needle distal opening can contact a contacting element (e.g., contacting element 1b which can be circular or any other suitable shape) at the distal end of the syringe barrel. In any of the embodiments herein, the contacting element can be distal to the distal seal and can be configured to contact a subject. The contacting element is optional and the distal seal can function as a contacting element herein. In any of the embodiments herein, the distal seal and/or the contacting element can be configured to prevent discharge of the flowable composition in the distal lumen through the needle distal opening. In other words, the flowable composition does not flow out of the needle distal opening when the needle distal opening contacts the distal seal and/or the contacting element.

In any of the embodiments herein, the needle base can be configured to advance the needle distally such that the needle distal opening is in a first tissue of a subject, when the needle body opening is in the distal lumen contacting the flowable composition. The first tissue can prevent discharge of the flowable composition in the distal lumen through the needle distal opening. In any of the embodiments herein, the pressure at the needle body opening is in the distal lumen is no greater than the pressure at the needle distal opening in the first tissue. In any of the embodiments herein, the distal lumen can be in fluidic communication with the needle distal opening through the needle body opening and the needle body passageway.

In any of the embodiments herein, the needle base can be configured to advance the needle distally such that the needle body opening is in the distal lumen while the needle distal opening is in a second tissue distal to the first tissue of the subject or between the first and second tissues. In any of the embodiments herein, the first tissue can be a surface tissue and the second tissue can be deeper tissue. In any of the embodiments herein, the needle distal opening can be in an apparent or potential tissue void, cavity, or vessel which can be in the second tissue or between the first and second tissues. In any of the embodiments herein, the pressure at the needle distal opening in the second tissue or between the first and second tissues can be lower than the pressure at the needle distal opening in the first tissue. In any of the embodiments herein, the pressure at the needle distal opening in the second tissue or between the first and second tissues can be lower than the pressure at the needle body opening in the distal lumen. In any of the embodiments herein, the distal lumen can be in fluidic communication with apparent or potential tissue void, cavity, or vessel, through the needle distal opening, the needle body passageway, and the needle body opening in the distal lumen. In any of the embodiments herein, the floating seal can be configured to move distally due to the elastic engagement, without requiring the needle base or the needle to move distally. In any of the embodiments herein, the elastic engagement can comprise one or more springs and/or one or more elastic sheaths. In any of the embodiments herein, the flowable composition in the distal lumen can be discharged through the needle distal opening into the second tissue or a void formed therein or between the first and second tissues. In any of the embodiments herein, the first tissue can be a sclera, the second tissue can be a choroid/ciliary body, and/or the void can be a suprachoroidal space.

In any of the embodiments herein, the flowable composition can comprise a liquid, a solution, a suspension, a gel, an oil, an ointment, an emulsion, a cream, a foam, a lotion, and/or a paste. In any of the embodiments herein, the space between the floating seal and the needle base may not comprise the flowable composition or any non-gas flowable composition. In any of the embodiments herein, the space between the floating seal and the needle base can comprise a gas such as sterilized air. In any of the embodiments herein, the space between the floating seal and the needle base can be connected to the outside of the syringe barrel, e.g., to the outside environment, such that the space is not a sealed space. In any of the embodiments herein, when the needle is in the space between the floating seal and the needle base, the needle can be covered by an elastic sheath. The elastic sheath can seal the needle body opening and can prevent the flowable composition from leaking into the space between the floating seal and the needle base. In any of the embodiments herein, the distal lumen may not comprise a gas and may comprise only a non-gas flowable composition, such as a pharmaceutical composition and/or a pharmaceutical acceptable carrier or excipient in the form of a liquid, a solution, a suspension, a gel, an oil, an ointment, an emulsion, a cream, a foam, a lotion, and/or a paste.

In any of the embodiments herein, the system may further comprise a linear member configured to advance distally through the needle. Optionally, all or a portion of the linear member may be exposed at a distal end of the needle. In any of the embodiments herein, the linear member can comprise a wire, a tube, or any combination thereof. In any of the embodiments herein, the linear member can be selected from the group consisting of a guidewire, a sheath, a catheter, a cannula, a microneedle, an electrode, and a sensor. In any of the embodiments herein, the system may further comprise a guiding member configured to guide the linear member toward, into and/or through the needle.

In any of the embodiments herein, at least one component of the system can be separately provided from one or more other components. In any of the embodiments herein, two or more components of the system can be made as one piece or preassembled.

In some embodiments, disclosed herein is a device comprising a syringe barrel comprising a proximal end (optionally a proximal open end) and a distal end (optionally a distal closed end); an actuation unit in the syringe barrel comprising a needle base and a floating seal elastically engaging each other, the needle base being proximal to the floating seal; a needle comprising a needle proximal end engaging the needle base and a needle distal end, the needle comprising: (i) a needle distal opening, (ii) a needle body opening between the needle proximal end and the needle distal end, the needle body opening being proximal to the needle distal opening, and (iii) a needle body passageway connecting the needle distal opening and the needle body opening. In any of the embodiments herein, the device can further comprise a flowable composition lumen distal to the floating seal. In any of the embodiments herein, the actuation unit can be configured to advance the needle to place the needle proximal end and/or the needle distal end in the flowable composition lumen.

In any of the embodiments herein, the flowable composition lumen can comprise a flowable composition selected from the group consisting of a liquid, a solution, a suspension, a gel, an oil, an ointment, an emulsion, a cream, a foam, a lotion, a paste, and any combination thereof. In any of the embodiments herein, the flowable composition lumen may not comprise a gas. In any of the embodiments herein, the space in the syringe barrel between the floating seal and the needle base may not comprise a flowable composition selected from the group consisting of a liquid, a solution, a suspension, a gel, an oil, an ointment, an emulsion, a cream, a foam, a lotion, a paste, and any combination thereof. In any of the embodiments herein, the space in the syringe barrel between the floating seal and the needle base can comprise a gas such as sterilized air. In any of the embodiments herein, the space between the floating seal and the needle base can be connected to the outside of the syringe barrel, e.g., to the outside environment, such that the space is not a sealed space.

In any of the embodiments herein, the needle base can engage an actuation member (e.g., pressing element) on the proximal open end of the syringe barrel, and the actuation member (e.g., pressing element) can be configured to advance the needle base and the needle distally. In any of the embodiments herein, the actuation unit can comprise an energy storage member elastically engaging the needle base and the floating seal. In any of the embodiments herein, the energy storage member can be a first energy storage member, the actuation unit can further comprise a second energy storage member elastically engaging a slider and the floating seal, and a portion of the slider can extend outside the syringe barrel. In any of the embodiments herein, the energy storage member can comprise a spring and/or an elastic sheath. In any of the embodiments herein, the energy storage member can be fixed to the needle base and/or the floating seal. In any of the embodiments herein, the energy storage member can be releasably connected to the needle base and/or the floating seal. In any of the embodiments herein, the energy storage member can be configured to exert a force on the floating seal which in turn exerts a force on a flowable composition in the flowable composition lumen. In any of the embodiments herein, the energy storage member can be configured to move the floating seal distally without moving the needle base or the needle.

In any of the embodiments herein, the device can comprise a sheath configured to enclose all or a portion of the needle. In any of the embodiments herein, the sheath can be configured to enclose the needle distal opening and/or the needle body opening. In any of the embodiments herein, the sheath can be configured to seal the needle body opening when enclosing the needle body opening.

In any of the embodiments herein, the device can comprise a stopper in the flowable composition lumen, and the stopper can be configured to stop the floating seal from moving distally. In any of the embodiments herein, the stopper can be provided on an inner wall of the syringe barrel enclosing the flowable composition lumen. In any of the embodiments herein, the device can comprise a distal seal at the distal closed end of the syringe barrel. In any of the embodiments herein, the floating seal, the syringe barrel, and the distal seal can enclose the flowable composition lumen.

In any of the embodiments herein, the device can comprise a contacting element at the distal closed end of the syringe barrel.

In any of the embodiments herein, the device can comprise a guiding structure configured to guide a linear member toward, into and/or through the needle. In any of the embodiments herein, the guiding structure can comprise an angled guiding groove on the floating seal. In any of the embodiments herein, the guiding structure can comprise a valve and/or a removable plug in the angled guiding groove. In any of the embodiments herein, the valve can be a one-way valve configured to open toward the needle. In any of the embodiments herein, the angled guiding groove can extend from a proximal surface of the floating seal to a distal surface of the floating seal. In any of the embodiments herein, the angled guiding groove may not extend through the floating seal.

In any of the embodiments herein, the device may further comprise the linear member. In any of the embodiments herein, the linear member can be selected from the group consisting of a guidewire, a sheath, a catheter, a cannula, a microneedle, an electrode, a sensor, and any combination thereof.

In some embodiments, disclosed herein is a device, comprising: (1) a first syringe unit comprising: a first syringe barrel; a needle base in the first syringe barrel; and a needle comprising a needle proximal end engaging the needle base and a needle distal end, the needle comprising: (i) a needle distal opening, (ii) a needle body opening between the needle proximal end and the needle distal end, the needle body opening being proximal to the needle distal opening, and (iii) a needle body passageway connecting the needle distal opening and the needle body opening; (2) a second syringe unit configured to engage a distal end of the first syringe unit, comprising: a second syringe barrel; and a floating seal in the second syringe barrel, and when the first and second syringe units are engaged, the floating seal is configured to elastically engage the needle base; and (3) a third syringe unit configured to engage a distal end of the second syringe unit, comprising a third syringe barrel enclosing a flowable composition, and the needle base can be configured to advance the needle to place the needle proximal end and/or the needle distal end in the flowable composition. In any of the embodiments herein, the device can comprise one or more syringe units, optionally a fourth syringe unit configured to engage a distal end of the third syringe unit.

In some embodiments, disclosed herein is a device, comprising: (1) a first syringe unit comprising: a first syringe barrel; a needle base and a floating seal in the first syringe barrel elastically engaging each other, the needle base being proximal to the floating seal; and a needle comprising a needle proximal end engaging the needle base and a needle distal end, the needle comprising: (i) a needle distal opening, (ii) a needle body opening between the needle proximal end and the needle distal end, the needle body opening being proximal to the needle distal opening, and (iii) a needle body passageway connecting the needle distal opening and the needle body opening; and (2) a second syringe unit configured to engage a distal end of the first syringe unit, comprising a second syringe barrel enclosing a flowable composition, and the needle base can be configured to advance the needle to place the needle proximal end and/or the needle distal end in the flowable composition. In any of the embodiments herein, the device can comprise one or more syringe units, optionally a third syringe unit configured to engage a distal end of the second syringe unit.

In some embodiments, disclosed herein is a device, comprising: (1) a first syringe unit comprising: a first syringe barrel; a needle base in the first syringe barrel; and a needle comprising a needle proximal end engaging the needle base and a needle distal end, the needle comprising: (i) a needle distal opening, (ii) a needle body opening between the needle proximal end and the needle distal end, the needle body opening being proximal to the needle distal opening, and (iii) a needle body passageway connecting the needle distal opening and the needle body opening; (2) a second syringe unit configured to engage a distal end of the first syringe unit, comprising: a second syringe barrel; a floating seal in the second syringe barrel, and when the first and second syringe units are engaged, the floating seal is configured to elastically engage the needle base; and a flowable composition, and the needle base can be configured to advance the needle to place the needle proximal end and/or the needle distal end in the flowable composition. In any of the embodiments herein, the device can comprise one or more syringe units, optionally a third syringe unit configured to engage a distal end of the second syringe unit.

In some embodiments, disclosed herein is a method comprising using the system or device of any of the embodiments disclosed herein, for placing the needle distal opening in a subject in need thereof. In some embodiments, the method comprises placing the needle distal opening in a first tissue of the subject, and the first tissue is capable of preventing discharge of a flowable composition through the needle distal opening. In any of the embodiments herein, the method can further comprise placing the needle distal opening in a second tissue or between the first and second tissues of the subject. In any of the embodiments herein, the needle distal opening can be in an apparent or potential tissue void, cavity, or vessel that allows discharge of a flowable composition through the needle distal opening. In any of the embodiments herein, the method can further comprise delivering a flowable composition through the needle distal opening to an apparent or potential tissue void, cavity, or vessel in the subject. In any of the embodiments herein, the method can further comprise implanting a wire or a tube through the needle distal opening in an apparent or potential tissue void, cavity, or vessel in the subject. In any of the embodiments herein, the apparent or potential tissue void, cavity, or vessel can comprise a suprachoroidal space, an epidural space, pleural cavity, peritoneal cavity, or articular cavity.

In some embodiments, disclosed herein is a method for placing a needle in a subject, comprising: (a) advancing the needle toward the subject to a first position, wherein: the needle is in a syringe barrel comprising a proximal end and a distal end, the needle comprises a needle proximal end engaging a needle base in the syringe barrel and a needle distal end, wherein the needle comprises: (i) a needle distal opening, (ii) a needle body opening between the needle proximal end and the needle distal end, wherein the needle body opening is proximal to the needle distal opening, and (iii) a needle body passageway connecting the needle distal opening and the needle body opening, wherein the needle base is proximal to a floating seal in the syringe barrel, the floating seal and the needle base are configured to elastically engage each other, and in the first position of the needle, the needle distal opening is proximal to the floating seal; and (b) advancing the needle toward the subject to a second position, wherein the needle body opening is proximal to the floating seal, wherein the needle distal opening is distal to the floating seal and in a lumen comprising a non-gas flowable composition, and wherein discharge of the non-gas flowable composition from the needle body opening is prevented.

In any of the embodiments herein, the method can further comprise: (c) advancing the needle toward the subject to a third position, wherein the needle body opening is distal to the floating seal and in the lumen comprising the non-gas flowable composition, wherein the needle distal opening contacts a distal seal, a contacting element, or a tissue of the subject, and wherein discharge of the non-gas flowable composition from the needle distal opening is prevented.

In any of the embodiments herein, the method can further comprise: (d) advancing the needle toward the subject to a fourth position, wherein the needle body opening is in the lumen comprising the non-gas flowable composition, wherein the needle distal opening is in an apparent or potential tissue void, cavity, or vessel of the subject, and wherein the floating seal is moved distally without further advancing the needle, thereby discharging the non-gas flowable composition through the needle body opening, the needle body passageway, and the needle distal opening into the apparent tissue void, cavity, or vessel or a tissue void formed from the potential tissue void. In any of the embodiments herein, the method can further comprise: (e) stopping further distal movement of the floating seal. In any of the embodiments herein, the further distal movement of the floating seal can be stopped by a stopper, or when the pressure in the lumen and the pressure in the apparent tissue void, cavity, or vessel or the tissue void formed from the potential tissue void reach equilibrium, or when the needle body opening is sealed by the floating seal.

In some embodiments, disclosed herein is a system, comprising: a syringe barrel comprising a proximal end and a distal end; a floating seal in the syringe barrel; a needle base proximal to the floating seal, a piston rod between the floating seal and the needle base, the needle base and the piston rod elastically engaging each other; and a needle in the piston rod, the needle comprising a needle proximal end engaging the needle base and a needle distal end, wherein the needle comprises: (i) a needle distal opening, (ii) a needle body opening between the needle proximal end and the needle distal end, wherein the needle body opening is proximal to the needle distal opening, and (iii) a needle body passageway connecting the needle distal opening and the needle body opening, wherein the needle base is configured to advance the needle distally through the piston rod and toward and/or through the floating seal.

In any of the embodiments herein, the floating seal can be fixedly attached to the distal end of the piston rod and form a sliding and sealing engagement with an inner surface of the syringe barrel. In any of the embodiments herein, the needle base can fixedly engage an actuation member (e.g., pressing element), and a spring can engage the actuation member and the piston rod, thereby providing the elastic engagement between the needle base and the piston rod.

In any of the embodiments herein, advancement of the needle distally through the piston rod and through the floating seal can occur without moving the floating seal distally, when the needle distal opening is in a tissue or an apparent or potential tissue void, cavity, or vessel providing a higher pressure at the needle distal opening than the pressure at the needle body opening. In some embodiments, the tissue resistance or tissue pressure does not allow injection of the flowable composition through the needle distal opening into the tissue, and the floating seal (as well as the piston rod in embodiments that have one) is not moved distally under a force from the spring, even though the needle can be advanced distally under a force from the pressing shaft. For instance, when the tissue pressure does not allow injection, a needle distal opening of the needle can be in the tissue while a needle body opening is distal to the floating seal and contacting the flowable composition. The floating seal can maintain its position in an axial direction while the needle is further advanced until the needle distal opening reaches an apparent or potential tissue void, cavity, or vessel.

In any of the embodiments herein, the floating seal can be moved distally, when the needle distal opening is in a tissue or an apparent or potential tissue void, cavity, or vessel providing a lower pressure at the needle distal opening than the pressure at the needle body opening. In some embodiments, the tissue resistance or tissue pressure allows injection of the flowable composition through the needle distal opening into the tissue, and the floating seal (as well as the piston rod in embodiments that have one) is moved distally under a force from the spring, and the needle does not need to be advanced distally. For instance, when the tissue pressure allows injection, a needle distal opening of the needle can be in the apparent or potential tissue void, cavity, or vessel, while a needle body opening is distal to the floating seal and contacting the flowable composition. The floating seal can be moved distally and the flowable composition is discharged from the needle distal opening while the needle is not further advanced distally.

In some embodiments, disclosed herein is a method of delivering a flowable composition into an eye of a subject using a system disclosed herein, comprising inserting the needle distal opening at a location of the eye and into a position between the sclera and the choroid/ciliary body of the eye, whereby the flowable composition enters the needle body opening, is passed through the body passageway, and is discharged from the needle distal opening. In some embodiments, the flowable composition is discharged in a suprachoroidal space in the eye. In some embodiments, the method comprises inserting a cannula at a location of the eye into the suprachoroidal space and advancing a distal tip of the cannula to a posterior segment of the eye. In some embodiments, the method comprises advancing a microneedle through the cannula such that a distal end of the microneedle pierces the choroid and/or ciliary body of the eye without piercing the retina of the eye. In some embodiments, the method comprises delivering a composition through the microneedle and into a subretinal space.

BRIEF DESCRIPTION OF THE DRAWINGS

The drawings illustrate certain embodiments of the features and advantages of this disclosure. These embodiments are not intended to limit the scope of the appended claims in any manner.

FIG. 2F shows steps of operating an exemplary medical puncturing device without a contacting member (e.g., 1b shown in FIGS. 2A-2E), where a distal seal (e.g., 8 shown in FIGS. 2A-2E) may directly contact a tissue. FIG. 2G shows steps of operating an exemplary medical puncturing device comprising an additional actuation member 2' engaging floating seal 3 via another spring 4', whereas actuation member 2 engages floating seal 3 via spring 4.

FIGS. 3A-3F are partial structure diagrams of exemplary medical puncturing devices comprising floating seal 3 and one or more needle body openings (6b or 6b1, 6b2, and/or 6b3) and needle distal opening 6a.

FIG. 8 shows a partial structure diagram of an exemplary medical puncturing device comprising a non-through angled guiding groove 3a.

FIG. 11A shows contacting member 1b that contacts a tissue, while FIG. 11B shows distal seal 8 that contacts a tissue without an intervening contacting member.

Figure 1A:
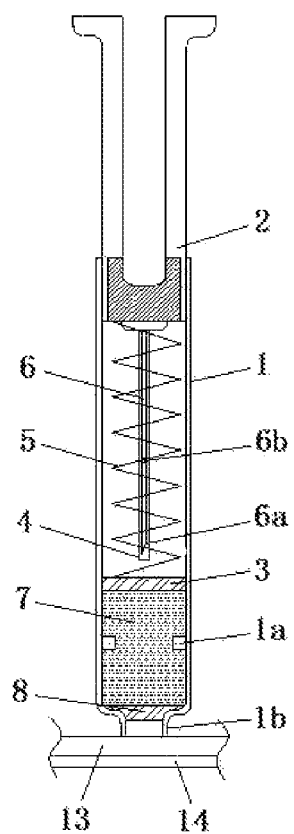
FIGS. 1A-1E show schematic diagrams of the different stages of operating an exemplary medical puncturing device, for example, during the punctuation and injection of suprachoroidal space (SCS) 14.
Figure 1B:
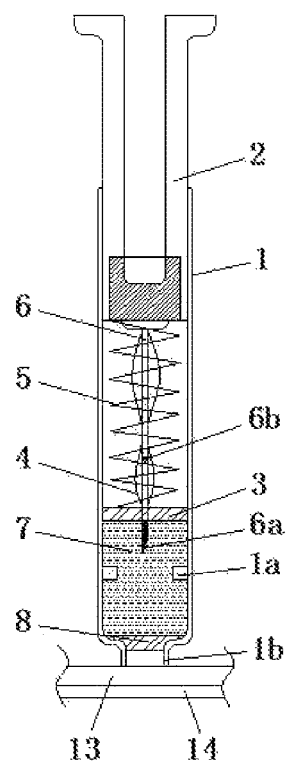
Figure 1C:
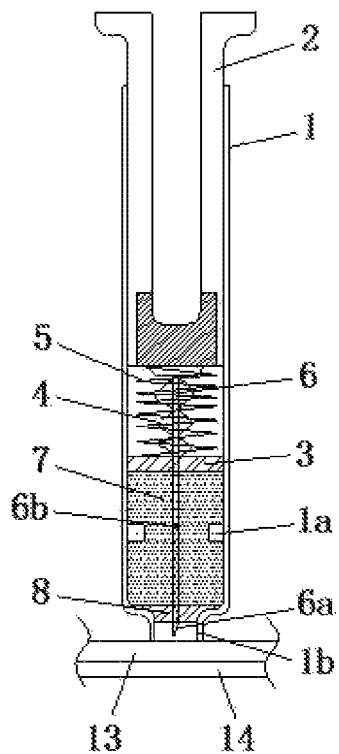
Figure 1D:
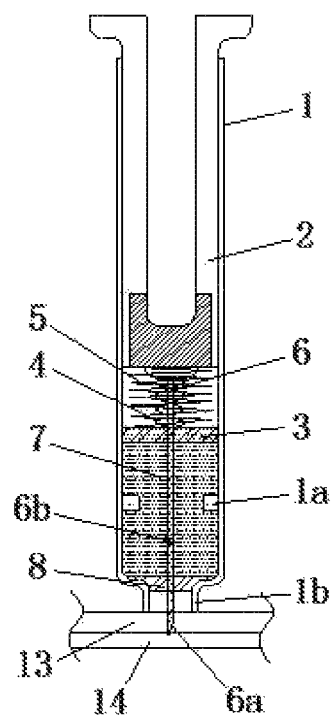
Figure 1E:
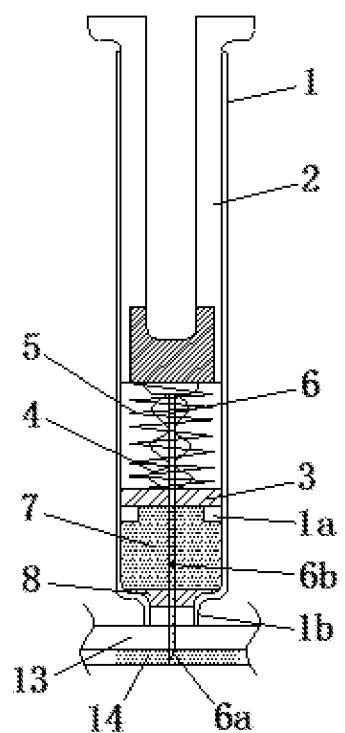
Figure 1F:
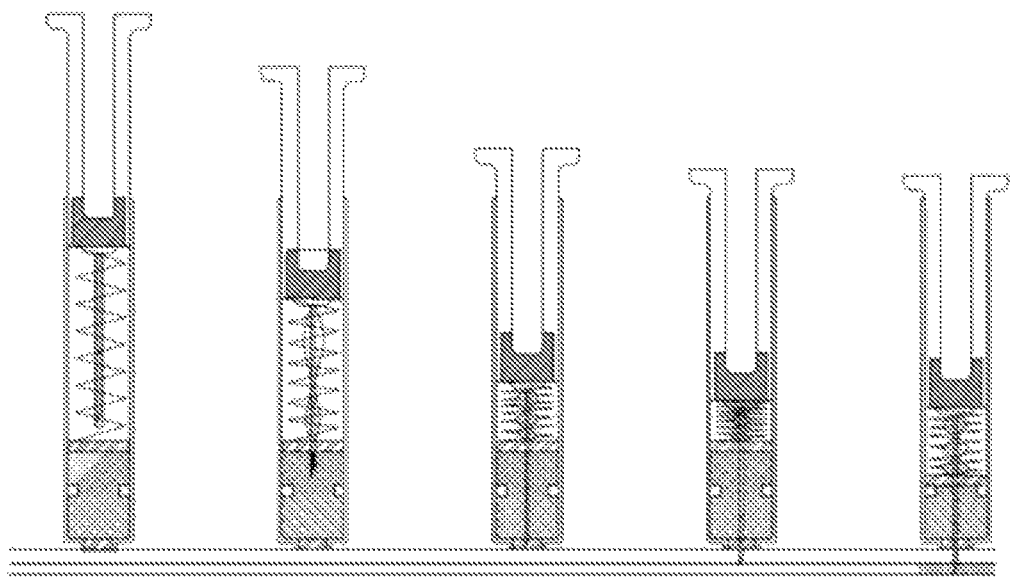
FIG. 1F show steps of operating an exemplary medical puncturing device without a contacting member (e.g., 1b shown in FIGS. 1A-1E), where a distal seal (e.g., 8 shown in FIGS. 1A-1E) may directly contact a tissue.

Reference numerals and exemplary corresponding structures are provided below for illustration only, for instance, with reference to FIGS. 1A-1E through FIGS. 11A-11B, and should not be considered limiting: 1—syringe barrel; 1a—axial stopper; 1b—circular contacting element; 2—pressing element; 2c—central guiding groove; 3—floating seal; 3a—angled guiding groove; 4—elastic sheath; 5—spring; 6—hollow puncture needle; 6a—needle distal opening; 6b—needle body opening; 6c—angled guiding needle hole; 7—flowable composition lumen; 8—distal seal; 9—one-way valve; 10—needle hole plug; 11—catheter; 12—auxiliary guiding needle; 13—sclera; 14—suprachoroidal space (SCS).

Figure 12:
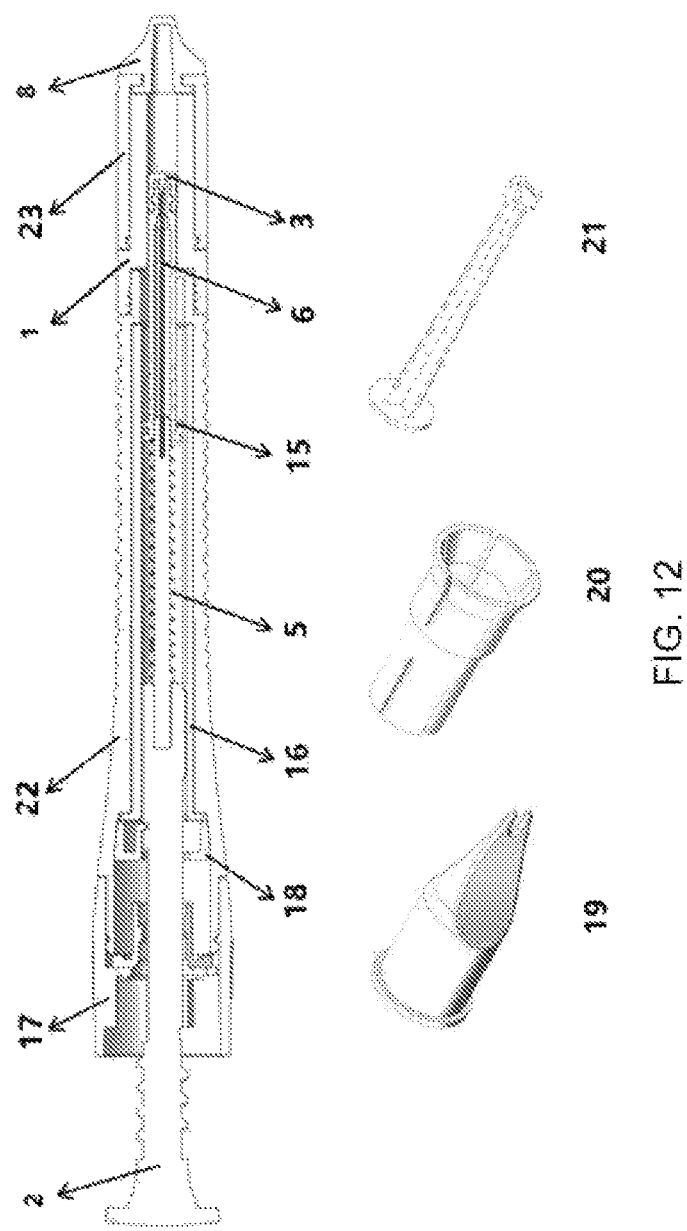

FIG. 12 shows schematic diagrams of various elements and features of an exemplary medical puncturing device. For instance, the device can comprise a hollow housing 22 engaging a proximal control knob 17. A pressing/push shaft 2 slidably passes through the control knob and engages a guide tube 16 inside the housing. The pressing/push shaft 2 is configured to provide a distally directed force on a compression spring 5, which in turn serves as a force element configured to provide a distally directed force on a piston rod 15. A beveled needle 6, is attached and fixed to a needle base or seat fixed to the pressing/push shaft. The distal end of the needle 6 can reside within a lumen of the piston rod 15 and move distally when a force is applied to move the pressing/push shaft distally. The distal end of the needle can be advanced to pass through a seal 3 at the distal end of the piston rod 15 into a lumen formed by a syringe barrel of a syringe 1 and a distal seal 8. A gland 23 may engage both the syringe 1 and the distal seal 8 to facilitate a sealing engagement. The distal seal 8 can interface a tissue, and the needle 6 can be advanced to pass through the distal seal 8 to penetrate the tissue. The needle 6 may comprise a needle distal opening and a needle body opening, similar to 6a and 6b respectively, as shown and used as described in FIGS. 1A-1E through FIGS. 11A-11B.

FIGS. 13A-13F show schematic diagrams of the different stages of operating an exemplary medical puncturing device.

Figure 13A:
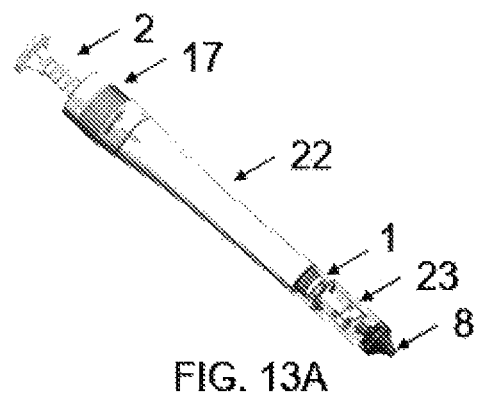
Figure 13B:
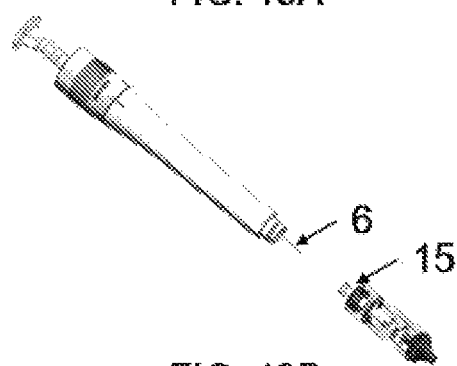
Figure 13C:
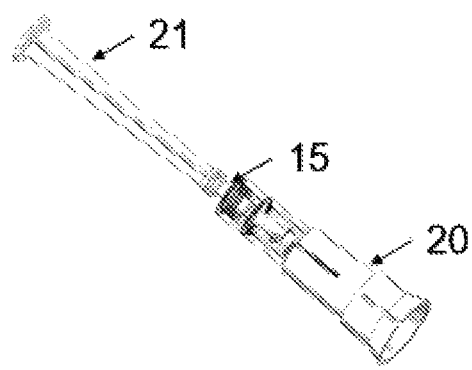
Figure 13D:
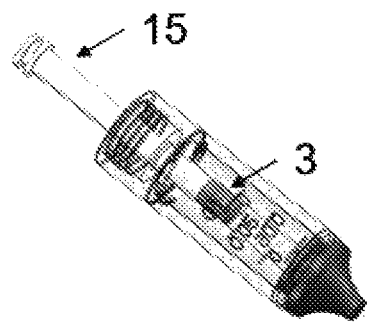
Figure 13E:
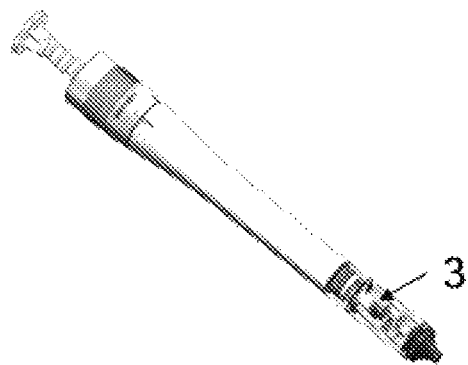
Figure 13F:
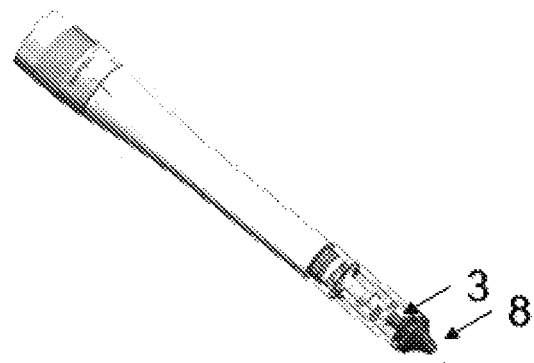
Figures 14A, 14B:
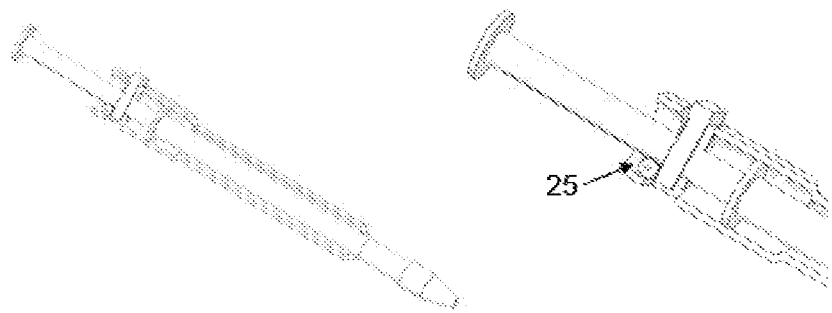

FIGS. 14A-14B show schematic diagrams of features of an exemplary engagement between the pressing shaft (e.g., pressing element 2 in FIGS. 1A-1E through FIGS. 11A-11B or pressing shaft 2 in FIG. 12 and FIGS. 13A-13F) and the control knob or key. FIG. 14A shows the exemplary device including the device body and the syringe and the distal seal at the distal end. FIG. 14B shows an enlarged view of the gear engagement that connects the pressing shaft and the control knob or key via one or more gears (e.g., gear 25). The control knob or key can be in the form of a button or a scroll wheel. The button can be pressed and the scroll wheel can be scrolled or rotated around an axis to actuate the pressing shaft via the one or more gears, thereby translating the syringe needle distally or proximally.

Figures 15A, 15B:
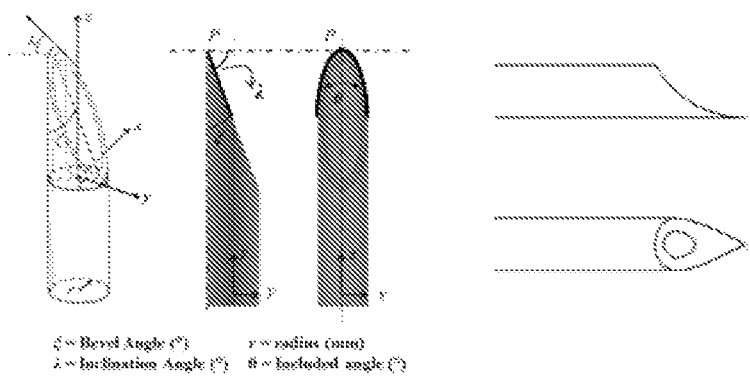

FIGS. 15A-15B show schematic diagrams of features of exemplary needles (e.g., hollow puncture needle 6 in FIGS. 1A-1E through FIGS. 11A-11B or syringe needle 6 in FIG. 12 and FIGS. 13A-13F).

Figures 16A, 16B, 16C:
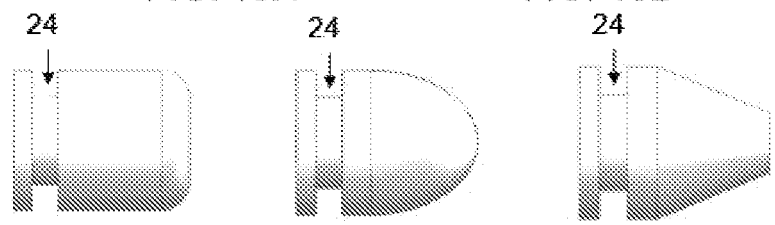

FIGS. 16A-16C show schematic diagrams of features of exemplary seals (e.g., distal seal 8 in FIGS. 1A-1E through FIGS. 11A-11B or sealing tip 8 in FIG. 12 and FIGS. 13A-13F) that are configured to contact a tissue, e.g., the sclera of an eye. The seal can have a cone-shaped distal portion, a spherical distal portion, or a flat distal portion. The seal can have a distal portion having a flat distal surface, a convex surface, a spherical surface, a concave surface, or a distal surface of any other suitable shape.

Reference numerals and exemplary corresponding structures are provided below for illustration only, for instance, with reference to FIG. 12 through FIGS. 16A-16C, and should not be considered limiting: 1—syringe having a syringe barrel forming a lumen; 2—pressing element (e.g., pressing shaft); 3—floating seal (e.g., plunger seal); 5—elastic element such as a spring; 6—hollow puncture needle (needle distal opening and needle body opening not shown); 8—distal seal; 15—piston rod (e.g., push rod); 16—guide tube; 17—control knob; 18—limiter; 19—ruler; 20—adapter; 21—handle; 22—housing; 23—gland; 24—annular groove; 25—gear.

Figure 17A:
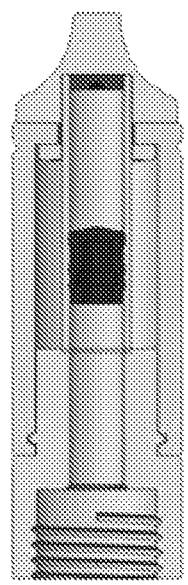
Figure 17B:
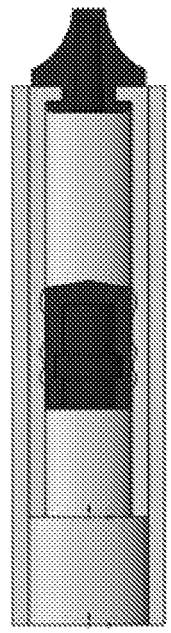

FIGS. 17A-17B show schematic diagrams of features of exemplary containers that can be prefilled with a flowable composition and installed in the device.

Figure 18:
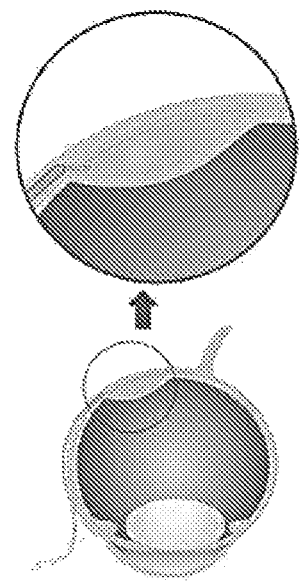
Figure 18:
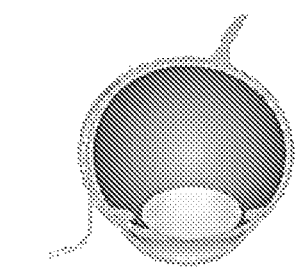
Figure 18:
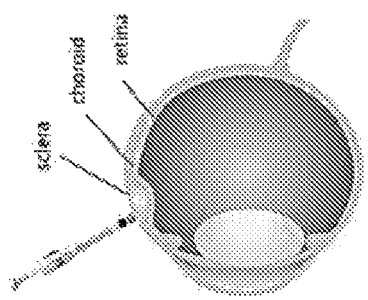

FIG. 18 shows schematic diagrams of an exemplary method using a device disclosed herein to facilitate subretinal delivery of a substance through a suprachoroidal space.

DETAILED DESCRIPTION

Below is a detailed description of some embodiments of the present disclosure. It should be understood that the specific implementations described herein are meant to illustrate and explain the embodiments of the present disclosure, and should not be considered limiting.

It should be noted that, when not in conflict, the embodiments of the present disclosure and the features of the embodiments may be combined in any suitable manner.

In some embodiments, the positional descriptions of "front," "back," "forward," "backward," "distal," and "proximal," etc. are based on the perspective of an operator of the medical puncturing device or medical apparatus assembly. That is, when the operator is using the medical puncturing device or medical apparatus assembly, the direction pointing away and relatively far from the operator is the forward direction, and the direction pointing toward and relatively close to the operator is the backward direction.

As used herein, the words "proximal" and "distal" refer to the direction closer to and away from, respectively, an operator (e.g., surgeon, physician, nurse, technician, etc.) who would insert the medical device into the patient, with the tip-end (distal end) of the device inserted inside a patient's body first. Thus, for example, the end of a needle (e.g., microneedle) described herein first inserted inside the patient's body would be the distal end, while the opposite end of the needle (e.g., the end of the medical device being manipulated by the operator) would be the proximal end of the needle.

As used herein, the singular forms "a," "an," and "the" include plural referents unless the context clearly dictates otherwise. For example, "a" or "an" means "at least one" or "one or more." Likewise, the term "a member" is intended to mean a single member or a combination of members, "a material" is intended to mean one or more materials, or a combination thereof.

The term "about" or "approximately" as used herein refers to the usual error range for the respective value readily known to the skilled person in this technical field. Reference to "about" a value or parameter herein includes (and describes) embodiments that are directed to that value or parameter per se. For example, "about" can mean within 1 or more than 1 standard deviation, per the practice in the relevant field. Alternatively, "about" can mean a range of up to 20%, up to 10%, up to 5%, or up to 1% of a given value.

Throughout the present disclosure, various aspects are presented in a range format. It should be understood that the description in range format is merely for convenience and brevity and should not be construed as an inflexible limitation on the scope of the present disclosure. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the present disclosure. The upper and lower limits of these smaller ranges may independently be comprised in the smaller ranges, and are also encompassed within the present disclosure, subject to any specifically excluded limit in the stated range. Where the stated range comprises one or both of the limits, ranges excluding either or both of those comprised limits are also comprised in the present disclosure. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

As used herein, the terms "puncture member", and "puncturing member" are used interchangeably to refer to an article configured to pierce tissue layers and deliver a substance to a target tissue layer, for example, a needle or a microneedle.

As used herein, the terms "medicament container", and "medicament containment chamber" are used interchangeably to refer to an article (e.g., a syringe) configured to contain a volume of a substance, for example, a medicament or drug.

All publications, comprising patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Overview

The medical puncture device and medical appliance assembly of the present invention can be used for the penetration, expansion and/or injection of cavities such as the suprachoroidal cavity of the eye, as well as the implantation of drugs, catheters or other medical devices. At present, the most commonly used intraocular injection method is intravitreal injection, but some drugs or gene therapy vectors penetrate the posterior vitreous membrane and the inner layer of the retina to reach the outer layer of the retina or the retinal pigment epithelium layer with low efficiency. In addition, because the vitreous cavity is a semi-open cavity, the drugs injected into the vitreous cavity are likely to flow out of the eyeball with the circulation of aqueous humor, which affects the local concentration and pharmacokinetics of the drug, and may also cause side effects such as increased intraocular pressure and cataracts. In some cases, in order to enable the drug or gene therapy vector to reach an effective concentration in the outer layer of the retina, the retinal pigment epithelium and/or the choroid/ciliary body, a hollow puncture needle can be used. The hollow puncture needle can penetrate the retina on the side of the vitreous cavity to reach the subretinal tissue, or the hollow needle can penetrate the retina and the retinal pigment epithelium to the subcutaneous space of the retinal pigment epithelium, and then inject drugs or gene therapy vectors. This type of injection is difficult and is prone to injection failure. In contrast, suprachoroidal injection can achieve a higher drug concentration in the choroid/ciliary body, retinal pigment epithelium and/or outer layer of the retina, and the vitreous drug concentration is lower.

In some instances, targeted injection of a therapeutic agent is desirable. In such instances, however, the relatively small anatomic structures of the eye often result in significant challenges to placing a needle at a target location using known devices and methods, especially as they pertain to placing the distal end of the needle at the desired depth within the eye. Many known methods of direct injection of a drug into the eye include inserting a needle or a cannula at an acute angle relative to a surface of the eye, which can make controlling the depth of insertion challenging. For example, some such methods include controlling the angular orientation of the needle such that the injected substance exits the needle at a particular location. Moreover, some known methods of injecting substances into ocular tissue include using complicated visualization system or sensors to control the placement of the needle or cannula.

Such shortcomings in known systems and methods are exacerbated because the size and thickness of various layers included in the eye can vary substantially from one person to another. For example, the thickness of the conjunctiva and the sclera can be substantially different and their true value cannot easily be predetermined via standard techniques. Furthermore, the thickness of these layers can also be different in different portions of the eye and at different times of the day in the same eye and location. Therefore, using known systems and methods it can be challenging to determine and/or adjust the length of the needle for puncturing the eye, such that a tip of the needle is at the desired depth, for example, the SCS.

In some cases, such as choroidal melanoma, precise targeted injection of therapeutic agents into the suprachoroidal space may improve efficacy and reduce side effects. However, for the eye, its structure is small, and it is quite difficult to use existing devices or methods to realize the penetration, expansion, injection, or catheter placement of the suprachoroidal space, especially for medical devices such as catheters, especially when the device needs to be placed in a specific location in the suprachoroidal space.

Some puncture methods for the suprachoroidal space are to make the length of the exposed puncture needle equal to the thickness of the sclera. After the puncture needle is completely inserted into the sclera, fluid is injected to achieve the suprachoroidal injection. The technical disadvantage of this puncture method is that the exposed length of the reserved puncture needle may not be exactly the same as the thickness of the sclera. In practical applications, the difference in the thickness of the sclera between different people, between eyes, and between different parts of the same eye will further amplify the above technical defects. Too short a needle might not penetrate the sclera, and too long a needle can traverse beyond the SCS and damage the retina of the eye. A convenient way to detect the position of the needle tip within the eye is needed.

Because of the sensitivities associated with intraocular injection (e.g., the sensitivity of the tissue, the potential impact on intraocular pressure and the like), many known systems involve manual injection. More particularly, many known devices and methods include the user manually applying a force (e.g., via pushing a plunger with their thumb or fingers) to expel a fluid (e.g., a drug) into the eye. Because of the small needle size and/or the characteristics of the injected drug, some such devices and methods involve the use of force levels higher than that which users are comfortable with applying, and in certain situations a user may not properly deliver the medicament using known systems and methods.

Moreover, injection into different target layers of the eye can cause variability in the amount of the force required for insertion of the needle and/or injection of the medicament. Different layers of the eye can have different densities. For example, the sclera generally has a higher density than the conjunctiva or the SCS. Differences in the density of the target region or layer can produce different backpressure against the needle exit, e.g., the tip of the needle from which the fluid emerges. Thus, injection into a relatively dense ocular material such as sclera requires more motive pressure to expel the medicament from the needle than is required when injecting a medicament into the SCS. Furthermore, the injection force to expel the medicament also depends on the density and viscosity of the liquid medicament, length of the needle, and diameter of the needle. To inject certain medicaments into the eye via desired needles (e.g., 27 gauge, 30 gauge, or even smaller) can require force which may be difficult to estimate and/or control in order to achieve proper injection without risking damage to eye tissues of a particular subject.

Given the relatively small anatomic structures of the eye, it has remained challenging to access certain internal regions of the eye, for example, in order to place a tube (e.g., a catheter) or wire at a desired region in a minimally invasive fashion.

The issues associated with accessing tissues in the eye may be applicable to other tissues as well. Thus, a need exists for improved devices and methods, which can assist in determining if the needle is at the correct depth, can facilitate injection of the medicament into tissues such as an ocular tissue, and/or can facilitate the implant of certain structures in tissues such as an ocular tissue.

In order to achieve one or more of the purposes mentioned above, the present disclosure provides in a medical puncturing device comprising:

- a syringe barrel, wherein the syringe barrel comprises a distal closed end and a proximal open end;
- an actuation unit (e.g., an elastic movement unit) comprising an actuation member (e.g., pressing element) and a floating seal, wherein the floating seal is positioned inside the syringe barrel and can elastically engage with the actuation member (e.g., pressing element);
- a hollow puncture needle attached to the actuation member (e.g., pressing element), wherein the hollow puncture needle comprises a needle distal opening and a needle body opening, and wherein the needle body opening is proximal to the floating seal (the needle distal opening can be proximal to the floating seal, e.g., the entire length of the needle is proximal to the floating seal, or alternatively, the needle can be through the floating seal such that the needle distal opening is distal to the floating seal); and
- a flowable composition lumen (e.g., for a fluid or gel), wherein the flowable composition lumen is formed by the syringe barrel distal closed end, a syringe barrel lumen wall (e.g., a portion of the syringe barrel), and the floating seal.

Figure 2A:
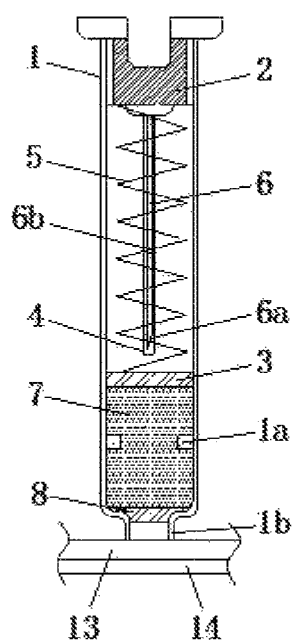
FIGS. 2A-2G show schematic diagrams of the different stages of operating an exemplary medical puncturing device, for example, during the punctuation and injection of suprachoroidal space (SCS) 14.
Figure 2B:
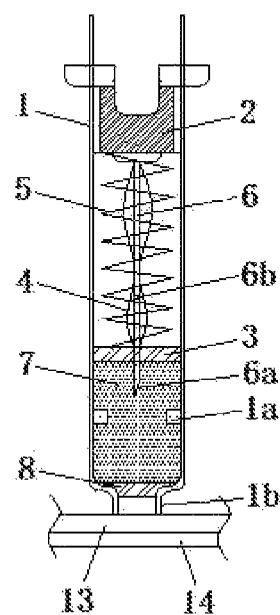
Figure 2C:
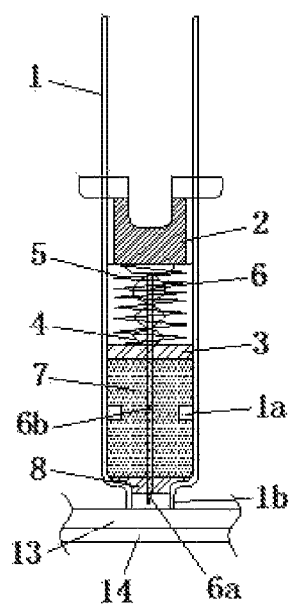
Figure 2D:
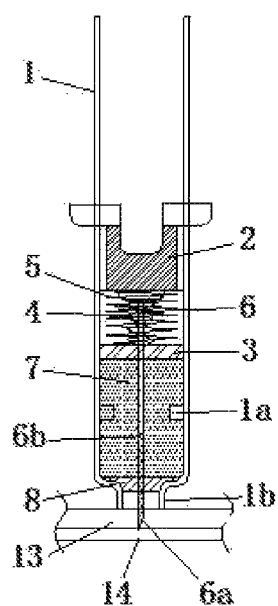
Figure 2E:
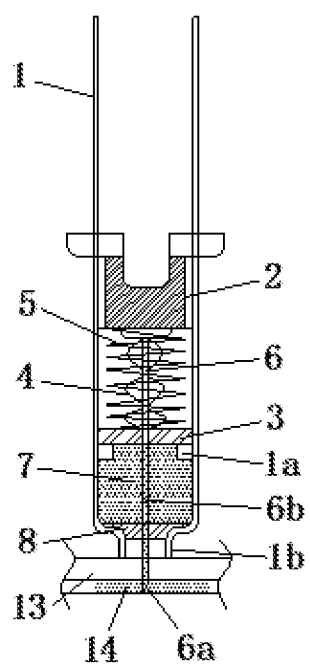
Figure 2F:
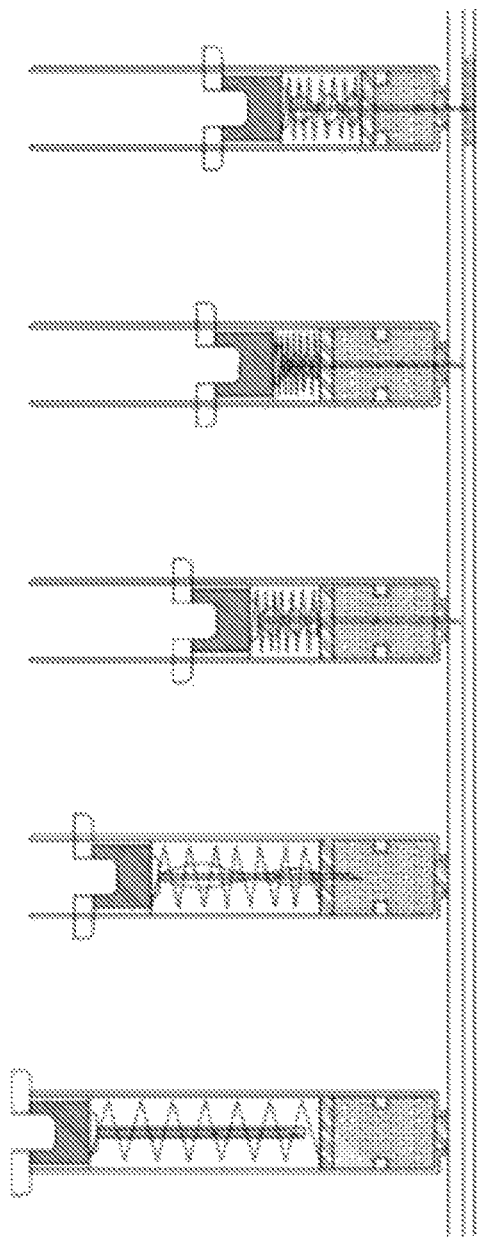
Figure 2G:
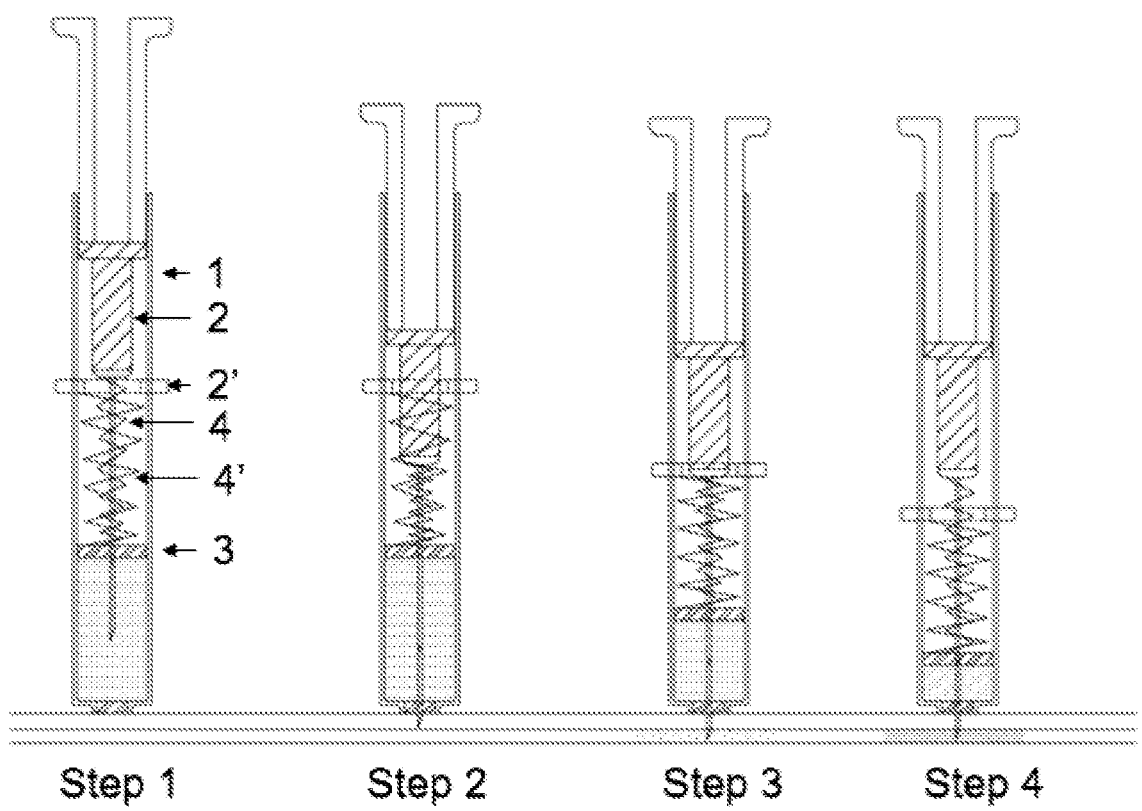
Figures 3A, 3B:
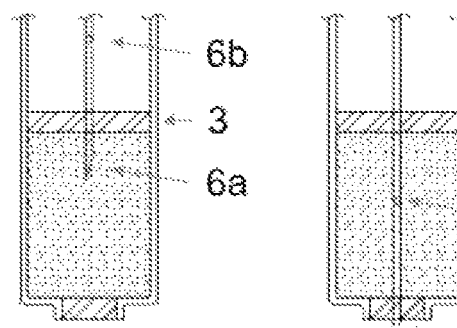
Figures 3C, 3D, 3E, 3F:
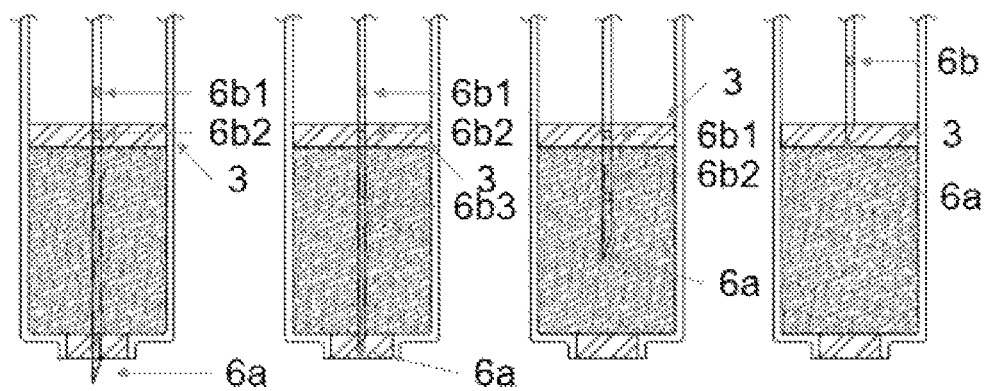

In some embodiments, the medical puncturing device is configured such that the hollow puncture needle can be moved forward by pressing the actuation member (e.g., pressing element). In some embodiments, the hollow puncture needle sequentially pierces the floating seal and the syringe barrel distal closed end, thus connecting the flowable composition lumen, the needle body opening, and the needle distal opening. In some embodiments, the hollow puncture needle is pre-inserted into the floating seal. For example, the needle distal opening can be in the floating seal and blocked by the floating seal, and the needle can be advanced through the flowable composition lumen to pierce the syringe barrel distal closed end. In some embodiments, the hollow puncture needle is pre-inserted through the floating seal. For example, the needle distal opening can be in the flowable composition lumen, while the needle body opening is proximal to the floating seal or in the floating seal (e.g., the needle body opening can be blocked by the floating seal as shown in FIG. 3E), and then the needle can be advanced to pierce the syringe barrel distal closed end. In some embodiments, the hollow puncture needle is pre-inserted through the floating seal and in or through the syringe barrel distal closed end. For example, the needle distal opening can be in a distal seal at the syringe barrel distal closed end (e.g., the needle distal opening can be blocked by the distal seal) or distal to the distal seal and/or the syringe barrel distal closed end, while the needle body opening is proximal to the floating seal (e.g., as shown in FIG. 3D, 6b1), in the floating seal (e.g., the needle body opening can be blocked by the floating seal as shown in FIG. 3D, 6b2), or in the flowable composition lumen (e.g., as shown in FIG. 3D, 6b3), and then the needle can be advanced through the syringe barrel distal closed end and exposing the needle distal opening for puncturing a tissue.

Optionally, the medical puncturing device comprises a state wherein the flowable composition lumen, the needle body opening, and the needle distal opening are in fluidic communication. For example, in a fluidic communication state, the needle body opening can be proximal to the floating seal, while the needle distal opening is distal to the floating seal and in the flowable composition lumen. In the fluidic communication state, the needle and/or the floating seal can be moved. For example, the floating seal can be moved under the elastic resilience between the floating seal and the actuation member (e.g., pressing element) such as that the floating seal seals or blocks the needle body opening, thereby preventing or terminating discharge of the flowable composition (such as a gel) from the needle body opening and/or from the needle distal opening.

Optionally, in the fluidic communication state, the floating seal can seal the needle body opening when it moves forward and contacts the syringe barrel distal closed end, thereby preventing or terminating discharge of the flowable composition (such as a gel) from the needle body opening and/or from the needle distal opening.

Optionally, a s stopper such as an axial stopper can be provided inside the syringe lumen, distal to the floating seal. In some embodiments, the stopper can be used to limit the forward movement of the floating seal. In some embodiments, the medical puncturing device comprises a fluidic communication state, wherein the flowable composition lumen is connected to the needle body opening and the needle distal opening. When the medical puncturing device is in the fluidic communication state, the needle body opening can be at the distal end of the stopper (e.g., as shown in FIG. 2D), and the floating seal can move forward due to the elastic engagement with the actuation member (e.g., pressing element).

Optionally, the medical puncturing device comprises a manual control element, which is attached to the floating seal and is extended outside of the syringe barrel.

Optionally, the medical puncturing device comprises a pre-puncture state after the hollow puncture needle pierces the syringe barrel distal closed end, a surface tissue puncture state, and a fluidic communication state after the puncture. In the pre-puncture state, the surface tissue puncture state, and the fluidic communication state, the length range of the hollow puncture needle extended outside of the syringe barrel distal closed end can correspond to a pre-puncture length range, a surface tissue puncture length range, and a fluidic communication length range, respectively, wherein: when the length of the of the hollow puncture needle extended outside of the syringe barrel distal closed end is within the pre-puncture length range, the needle body opening remains above the flowable composition lumen (e.g., the needle body opening can be proximal to and within the floating seal); and/or when the length of the of the hollow puncture needle extended outside of the syringe barrel distal closed end is within the surface tissue puncture length range, at least part of the needle body opening is connected to the flowable composition lumen; and/or when the length of the of the hollow puncture needle extended outside of the syringe barrel distal closed end is within the fluidic communication length range, the needle body opening is positioned within the flowable composition lumen.

Optionally, an axially extended circular contacting element is formed at the syringe barrel distal closed end, wherein the difference between the upper and lower limits of the pre-puncture length range equals to the axial length of the circular contacting element.

Optionally, the elastic movement unit comprises a elastic sheath covering the outside of the hollow puncture needle. When the needle body opening is proximal to the floating seal, the elastic sheath can seal the needle body opening. In some embodiments, when the flowable composition is a gel, it may not be necessary to seal the needle body opening when it is proximal to the floating seal.

Optionally, the medical puncturing device comprises a catheter guiding structure which is used to thread the catheter into a cavity (e.g., a needle body passageway connected to the needle distal opening and/or the needle body opening) of the hollow puncture needle.

Optionally, the catheter guiding structure comprises an angled guiding groove which is formed on the floating seal and extends towards the hollow puncture needle in an angle.

Optionally, the angled guiding groove is set to be through the floating seal in the front and back direction. In some embodiments, the catheter guiding structure further comprises a one-way valve which is embedded in the angled guiding groove and can be opened and closed, and/or a guiding groove plug inserted in the angled guiding groove.

Optionally, the angled guiding groove is set to be on the upper surface of the floating seal and is a non-through groove.

Optionally, the needle body opening is formed as an angled opening which opens obliquely backwards.

Optionally, the catheter guiding structure comprises an angled guiding needle hole formed on the body wall of the hollow puncture needle and opens obliquely backwards. In some embodiments, the medical puncturing device comprises a fluidic communication state wherein the flowable composition lumen is in connection with the needle body opening and the needle distal opening. In the fluidic communication state, the angled guiding needle hole is positioned proximal to the floating seal.

Optionally, the catheter guiding structure further comprises a one-way valve which is embedded in the angled guiding needle hole and can be opened and closed, or a guiding groove plug inserted in the angled guiding needle hole.

Optionally, the catheter guiding structure comprises a puncturable central guiding groove that is formed on the center of the proximal surface of the actuation member (e.g., pressing element). In some embodiments, a needle proximal opening is formed on the hollow puncture needle and the needle proximal opening is set to axially align with the central guiding groove.

Optionally, the medical puncturing device comprises a puncture control module and a fluid storage module that are independently manufactured and formed, wherein: the puncture control module comprises a first syringe unit and the elastic movement unit and the hollow puncture needle provided inside the first syringe unit; the fluid storage module comprises a second syringe unit, the flowable composition lumen formed inside the barrel of the second syringe unit, and a module packaging component which is removably packaged to the proximal end of the second syringe unit; and a removable connection structure is formed between the first syringe unit and the second syringe unit.

In a second aspect, the present disclosure provides a medical apparatus assembly. In some embodiments, the medical apparatus assembly comprises a catheter and the medical puncturing device comprising a catheter guiding structure.

Optionally, the medical apparatus assembly further comprises a hollow auxiliary guiding needle which is matched to use with the catheter guiding structure. In some embodiments, when the auxiliary guiding needle is connected to the catheter guiding structure, the catheter can sequentially go through the needle body passageway of the auxiliary guiding needle and the catheter guiding structure and be threaded into the needle body passageway of the hollow puncture needle.

In some embodiments, when using the medical puncturing device of the present disclosure, a user can first apply pressure to the actuation member (e.g., pressing element) to drive the hollow puncture needle sequentially through the floating seal and the syringe barrel distal closed end. When the needle distal opening of the hollow puncture needle reaches apparent or potential tissue gaps, cavity systems, and vessels, the needle body opening has already been positioned in the flowable composition lumen, and the floating seal has already formed an elastic engagement with the actuation member (e.g., pressing element). In some embodiments, the fluid pressure in the flowable composition lumen can be made higher than the pressure inside the an apparent or potential tissue void, cavity, or vessel.

At this time, the fluid inside the flowable composition lumen can flow into the an apparent or potential tissue void, cavity, or vessel through the needle body opening and the needle distal opening. During the injection process, just by maintaining the position of the actuation member (e.g., pressing element), under the action of the elastic engagement between the floating seal and the actuation member (e.g., pressing element), the fluid inside the flowable composition lumen can flow into the needle body opening (and then through the needle body passageway and out of the needle distal opening), thereby achieving injection, penetration, and/or expansion of the an apparent or potential tissue void, cavity, or vessel. Additionally, the medical apparatus assembly as describe in the present disclosure can achieve implantation of catheter and other medical device through the medical puncturing device, e.g., through a catheter guiding structure and a cavity of the needle described herein.

In some embodiments, before the hollow puncture needle pierces into an apparent or potential tissue void, cavity, or vessel, the external pressure on the needle distal opening is higher than the fluid pressure in the flowable composition lumen, thus fluid cannot flow out of the needle distal opening. Thus, by observing whether the floating seal moves forward due to the elastic engagement with the actuation member (e.g., pressing element), it is possible to determine whether the hollow puncture needle has already pierced into an apparent or potential tissue void, cavity, or vessel, thereby reminding the operator of the current punctuation depth to ensure accurate puncture. Since the injection is controlled by fluid pressure changes in the flowable composition lumen, the injection process does not require an operator to manually apply thrust or force during the injection process, thus fluctuations in the flow speed can be prevented and stable injection can be achieved.

Other features and advantages of the present disclosure will be described in the detailed description below.

Some embodiments of the present disclosure will be described with reference to the several views of the accompanying drawings.

II. Systems and Devices

In some embodiments, described herein are systems and devices to assist in the insertion of a puncture member, for example, a needle or microneedle into the eye, and/or assist in injecting a medicament into a target ocular tissue. In some embodiments, described herein are systems and devices for controlling the insertion depth of a puncture member, such as, for example, a microneedle, into the eye to deliver a therapeutic agent to, for example, a posterior region of the eye (e.g., via the suprachoroidal space). In some embodiments, described herein are systems and devices for introducing an implant into a tissue, such as an apparent or potential tissue void, cavity, or vessel.

In some embodiments, provided herein is a system comprising a syringe barrel comprising a proximal end and a distal end; a floating seal in the syringe barrel; a needle base proximal to the floating seal (e.g., the needle base is closer to an operator while the floating seal is closer to a subject), and the floating seal and the needle base are configured to elastically engage each other. In some embodiments, the system further comprises a needle comprising a needle proximal end and a needle distal end, and the needle proximal end engages the needle base. In any of the embodiments herein, the needle proximal end can be fixed to the needle base or releasably attached to (e.g., inserted in) the needle base. In any of the embodiments herein, the needle can comprise: (i) a needle distal opening, (ii) a needle body opening between the needle proximal end and the needle distal end, and (iii) a needle body passageway connecting the needle distal opening and the needle body opening. In any of the embodiments herein, the needle body opening can be proximal to the needle distal opening. In any of the embodiments herein, the needle base can be configured to advance the needle distally toward the floating seal (e.g., when the needle distal end is proximal to the floating seal), through the floating seal (e.g., when the needle distal end has entered or pierced into the floating seal), and/or through the distal end of the syringe barrel.

In any of the embodiments herein, a proximal lumen and a distal lumen can be provided in the syringe barrel on different sides of the floating seal. In some embodiments, the distal lumen comprises a flowable composition (e.g., a medicament, a drug, and/or a pharmaceutically acceptable carrier or excipient such as a saline), while the proximal lumen does not contain a non-gas flowable composition. The proximal lumen may be pre-filled with a gas, such as a sterilized air, and/or capable of communicating with the outside environment such as the atmosphere when the needle is advanced in and/or through the syringe barrel.

In some embodiments, the needles included in the embodiments described herein comprise a bevel, which allows for ease of penetration into a tissue such as the sclera and/or suprachoroidal space with minimal collateral damage. In some embodiments, the needles disclosed herein can define a narrow lumen (e.g., gauge size greater than or equal to 30 gauge, 32 gauge, 34 gauge, 36 gauge, etc.) to allow for suprachoroidal drug delivery while minimizing the diameter of the needle track caused by the insertion of the needle. In some embodiments, the lumen and bevel aspect ratio of the needles described herein are the same or different from standard 27 gauge and 30 gauge needles commonly used for intraocular injection.

In some embodiments, the needles included in the embodiments described herein are designed to quickly penetrate a dense tissue, such as the sclera, thereby placing the tip of the needle between the dense tissue and an adjacent, less dense tissue. For instance, the tip of a needle herein can be designed to quickly and precisely reach a suprachoroidal space without the risk of overshooting. In some embodiments, a syringe needle included in the embodiments described herein can be between about 20 gauge (G) and about 34 G, particularly between about 23 gauge (G) and about 30 G, such as between about 25 G and about 27 G. In some embodiments, a syringe needle disclosed herein can be 22 G, 23 G, 24 G, 25 G, 26 G, 27 G, 28 G, 29 G, 30 G, or 31 G. Exemplary needle sizes are shown in the Table 1 below.

TABLE 1

| Gauge | Needle Nominal O.D. (mm) | Needle Nominal I.D. (mm) | Needle Wall Thickness (mm) | Needle Dead Volume (μL/25.4 mm) |
|---|---|---|---|---|
| 34 | 0.159 | 0.051 | 0.051 | 0.052 μL/25.4 mm |
| 33 | 0.21 | 0.108 | 0.051 | 0.233 μL/25.4 mm |
| 32 | 0.235 | 0.108 | 0.064 | 0.233 μL/25.4 mm |
| 31 | 0.261 | 0.133 | 0.064 | 0.353 μL/25.4 mm |
| 30 | 0.312 | 0.159 | 0.076 | 0.504 μL/25.4 mm |
| 29 | 0.337 | 0.184 | 0.076 | 0.675 μL/25.4 mm |
| 28 | 0.362 | 0.184 | 0.089 | 0.675 μL/25.4 mm |
| 27 | 0.413 | 0.21 | 0.102 | 0.876 μL/25.4 mm |
| 26s | 0.474 | 0.127 | 0.178 | 0.322 μL/25.4 mm |
| 26 | 0.464 | 0.26 | 0.102 | 1.349 μL/25.4 mm |
| 25s | 0.515 | 0.153 | 0.178 | 0.464 μL/25.4 mm |
| 25 | 0.515 | 0.26 | 0.127 | 1.349 μL/25.4 mm |
| 24 | 0.566 | 0.311 | 0.127 | 1.93 μL/25.4 mm |
| 23s | 0.642 | 0.116 | 0.267 | 0.268 μL/25.4 mm |
| 23 | 0.642 | 0.337 | 0.152 | 2.266 μL/25.4 mm |
| 22s | 0.718 | 0.168 | 0.279 | 0.563 μL/25.4 mm |
| 22 | 0.718 | 0.413 | 0.152 | 3.403 μL/25.4 mm |
| 21 | 0.819 | 0.514 | 0.152 | 5.271 μL/25.4 mm |
| 20 | 0.908 | 0.603 | 0.152 | 7.255 μL/25.4 mm |

In some embodiments, a needle disclosed herein comprises a bevel angle between about 0 degree and about 40 degrees, particularly between about 5 degrees and about 30 degrees, such as between about 15 degree and about 25 degrees. In some embodiments, a syringe needle disclosed herein can comprise a bevel angle of about 10, about 12, about 14, about 16, about 18, about 20, about 22, about 24, about 26, about 28, or about 30 degrees. In some embodiments, a needle disclosed herein comprises an inclination angle between about 30 degrees and about 95 degrees, particularly between about 45 degrees and about 90 degrees, such as between about 60 degree and about 75 degrees. In some embodiments, a needle disclosed herein comprises an included angle between about 10 degrees and about 90 degrees, particularly between about 15 degrees and about 60 degrees, such as between about 20 degree and about 45 degrees. FIG. 15A shows the bevel angle, inclination angle, and included angle of a needle.

In some embodiments, a needle disclosed herein comprises a curved bevel. In some embodiments, the curved bevel has a curvature radius between about 0.1 mm and about 4.0 mm, particularly between about 0.2 mm and about 3.0 mm, such as between about 0.4 mm and about 2.0 mm. In some embodiments, a syringe needle disclosed herein can comprise a bevel having a curvature radius of about 0.5 mm, about 0.75 mm, about 1.0 mm, about 1.25 mm, about 1.5 mm, about 1.75 mm, or 2.0 mm, or between any of the aforementioned values.

In some embodiments, a needle disclosed herein comprises a multi-sided blade, for example, a two-sided blade, a three-sided blade, a four-sided blade, or a five-sided blade.

In some embodiments, a device disclosed herein comprises or is configured to be coupled to a medicament container containing a medicament, such as a solution, a liquid, a suspension, a gel, or the like. The medicament container can be formed at least in part by the syringe barrel.

Unlike certain existing devices in which a needle is coupled to a distal end of a medicament container (e.g., the needle is at the distal end of a syringe, for example, as described in U.S. Pat. Nos. 9,180,047, 9,539,139, 9,572,800, 9,636,253, 9,636,332, 9,770,361, 9,937,075, 10,555,833, and 10,517,756, which are incorporated herein by reference for all purposes), in some embodiments, the present disclosure utilizes a needle that is coupled to an actuation member inside a syringe barrel. In some embodiments, a need disclosed herein is at least partially inside the syringe barrel. In some embodiments, prior to use, the needle neither is exposed at the distal end of the syringe barrel nor directly engages the distal end of the syringe barrel.

In some embodiments, a device disclosed herein comprises an energy storage member (e.g., one or more springs) configured to engage the needle base and the floating seal. In some embodiments, a distal end portion of the energy storage member is configured to be disposed within the syringe barrel and directly or indirectly engage the floating seal. In some embodiments, the energy storage member is configured to produce a force on a proximal end portion of the floating seal. In some embodiments, the force is sufficient to move the floating seal within the syringe barrel to convey at least a portion of a substance from the medicament container (e.g., a flowable composition lumen) via the needle when a distal tip of the needle is disposed within an apparent or potential tissue void, cavity, or vessel. Furthermore, the force is insufficient to move the floating seal within the syringe barrel when the distal tip of the needle is disposed within a tissue adjacent to (e.g., above or below) the apparent or potential tissue void, cavity, or vessel. In some embodiments, the apparent or potential tissue void, cavity, or vessel has a first density and the adjacent tissue has a second density, higher than the first density. In some embodiments, the apparent or potential tissue void, cavity, or vessel produces a first backpressure and the adjacent tissue produces a second backpressure, higher than the first backpressure.

In some embodiments, a device disclosed herein comprises an energy storage member (e.g., one or more springs, e.g., spring 5 in FIGS. 1A-1E or FIG. 12) configured to exert a force on a floating seal directly (e.g., as shown in FIGS. 1A-1E) or indirectly (e.g., as shown in FIG. 12, via a piston rod 15). In some embodiments, the energy storage member is configured to exert a force on the floating seal that is between the pressure in a first tissue and the pressure in a second, less dense tissue or an apparent or potential tissue void, cavity, or vessel. In some embodiments, the energy storage member is configured to exert a force that is less than or equal to the pressure in the first tissue, but greater than the pressure in the second, less dense tissue or an apparent or potential tissue void, cavity, or vessel. In some embodiments, the energy storage member is configured to directly or indirectly exert a force on the floating seal, and the effect of the force is sufficient to overcome the pressure difference between the pressure at the needle distal opening in the sclera and the pressure at the needle distal opening in a suprachoroidal space. Due to the difference in pressure, once the needle distal opening advances through the first tissue and starts to enter the second, less dense tissue, the energy stored in the energy storage member is automatically released to advance the floating seal (e.g., via a piston rod 15 in FIG. 12), thereby discharging a volume of the flowable composition into the second tissue or in a void between the first and second tissues.

Unlike certain existing devices in which a needle is coupled to a floating seal, in some embodiments, the present disclosure utilizes a needle whose proximal end is coupled to an actuation member inside a syringe barrel, where the actuation member is separately provided and is proximal to the floating seal. In some embodiments, the proximal end of a need disclosed herein is not coupled to the floating seal. In some embodiments, prior to use, the needle can be distal to the floating seal or can be through the floating seal, but its proximal end of the needle remains distal to the floating seal and is not fixedly attached to the floating seal.

In certain existing devices, a medicament container (e.g., comprising a liquid) is provided between a proximal seal and a distal seal that each can move within a syringe barrel, for example, as described in US 2020/0069883 which is incorporated herein by reference for all purposes. In those devices, a force on the proximal side of the proximal seal is transmitted through the liquid to the distal seal which is attached to a needle. Given liquids are generally incompressible, when an operator uses too much force or applies a force abruptly on the proximal seal (e.g., through a plug coupled to the proximal seal), the force will be transmitted to the needle. With the liquid providing little compressibility to buffer the impact of the force, the needle may be inserted too deeply or too abruptly, causing damage to the target tissue (e.g., suprachoroidal space) and/or surrounding tissues. Although the positions of the proximal seal and the distal seal may be observed during injection, once a force that may cause overshooting of the needle is applied, it could already to be too late to stop the movement of the needle due to lack of the ability to buffer the impact of the force.

In contrast, in some embodiments of the present disclosure, the medicament container (e.g., flowable composition lumen) is provided between a floating seal and the distal end of a syringe barrel (where the distal end does not move relative to the syringe barrel). In some embodiments, the distal end of the syringe barrel comprises a distal seal and the flowable composition lumen is provided between the floating seal and the distal seal. In some embodiments, since the needle base is elastically connected to the floating seal (and therefore the flowable composition), the elastic connection can facilitate the operator to apply the right force and buffer the impact of that force. In addition, an operator can hold the needle base still relative to the syringe barrel and observe the movement of the floating seal in order to assess the depth of needle placement. Once fluidic communication is established between the flowable composition and an apparent or potential tissue void, cavity, or vessel, and the pressure in the flowable composition is greater than that in the apparent or potential tissue void, cavity, or vessel, the floating seal can move as the flowable composition enters the tissue, while the needle and the needle base do not have to move. Thus, precise needle placement and steady injection can be achieved and chances of needle overshooting can be effectively reduced or eliminated.

In some embodiments of the present disclosure, the medicament container (e.g., a syringe configured to contain a flowable composition) can be set to have an adjustable volume, e.g., between about 0 and about 0.2 mL, such as between about 0 and about 0.15 mL, particularly between about 0 and about 0.1 mL, including about 0.025 mL, about 0.05 mL, about 0.075 mL, about 0.1 mL, or between any of the aforementioned values. The volume of the flowable composition to be delivered (e.g., via injection) using a device disclosed herein can be selected based on the conditions of a particular subject, and can be adjusted according to changes in the conditions.

In some embodiments, a device disclosed herein is provided and/or packaged as an integrated device comprising components engaging each other. In some embodiments, a device disclosed herein does not require an operator to assemble one or more of components prior to use. In some embodiments, a device disclosed herein comprises a pre-filled medicament container (e.g., flowable composition lumen) comprising a flowable composition, such as a medicament in the form of a liquid, a solution, a suspension, a gel, an oil, an ointment, an emulsion, a cream, a foam, a lotion, and/or a paste.

Flowable compositions include liquid (e.g., solution, suspension, or the like) or semi-solid compositions (e.g., gels) that are easy to manipulate and may be injected, shaped and/or molded at or near the target tissue site as it coagulates. "Flowable" includes formulations with a low viscosity or water-like consistency to those with a high viscosity, such as a viscoelastic or a paste-like material. In some embodiments, a method disclosed herein involves injecting a viscoelastic material (e.g., a viscoelastic fluid) into an eye, e.g., between the sclera and the choroid/ciliary body of the eye in order to form a suprachoroidal space containing the viscoelastic material. In some embodiments, a viscoelastic fluid is are a non-Newtonian fluid formed by a viscous component and an elastic one, such as a blend of a solvent and a polymeric material. Examples of viscoelastic materials that can be used herein include sodium hyaluronate, Provisc (1% viscous and transparent material which is a specific fraction of sodium hyaluronate), Viscoat (a dispersive viscoelastic comprising of sodium hyaluronate and chondroitin sulphate), Amvisc (a purified fraction of sodium hyaluronate), Amvisc Plus (a 1.6% sodium hyaluronate product derived from rooster combs), sodium chondroitin sulfate/sodium hyaluronate, or DisCo Visc (4% sodium chondroitin sulfate, 1.65% sodium hyaluronate).

In various embodiments, the flowability of the formulation allows it to conform to irregularities, crevices, cracks, and/or voids in the tissue site. For example, in various embodiments, the formulation may be used to fill one or more voids, expand a tissue void (e.g., an apparent tissue void), and/or create a tissue void from a potential tissue void and optionally expand the created void. In some embodiments, upon contact with an aqueous medium (e.g., body fluid, water, etc.), the flowable composition may harden to form a drug depot that controls drug release.

In some embodiments, a therapeutic agent (e.g., a drug) is added to the flowable composition. Non-limiting examples of specific drugs and classes of drugs include β-adrenoceptor antagonists (e.g., carteolol, cetamolol, betaxolol, levobunolol, metipranolol, timolol), miotics (e.g., pilocarpine, carbachol, physostigmine), sympathomimetics (e.g., adrenaline, dipivefrine), carbonic anhydrase inhibitors (e.g., acetazolamide, dorzolamide), topoisomerase inhibitors (e.g., topotecan, irinotecan, camptothecin, lamellarin D, etoposide, teniposide, doxorubicin, mitoxantrone, amsacrine), prostaglandins, anti-microbial compounds, including anti-bacterials and anti-fungals (e.g., chloramphenicol, chlortetracycline, ciprofloxacin, framycetin, fusidic acid, gentamicin, neomycin, norfloxacin, ofloxacin, polymyxin, propamidine, tetracycline, tobramycin, quinolines), anti-viral compounds (e.g., acyclovir, cidofovir, idoxuridine, interferons), aldose reductase inhibitors, anti-inflammatory and/or anti-allergy compounds (e.g., steroidal compounds such as triamcinolone, betamethasone, clobetasone, dexamethasone, fluorometholone, hydrocortisone, prednisolone and non-steroidal compounds such as antazoline, bromfenac, diclofenac, indomethacin, lodoxamide, saprofen, sodium cromoglycate), artificial tear/dry eye therapies, local anesthetics (e.g., amethocaine, lignocaine, oxbuprocaine, proxymetacaine), cyclosporine, diclofenac, urogastrone and growth factors such as epidermal growth factor, mydriatics and cycloplegics, mitomycin C, and collagenase inhibitors and treatments of age-related macular degeneration such as pegagtanib sodium, ranibizumab, aflibercept and bevacizumab.

In one embodiment, the therapeutic agent is an integrin antagonist, a selectin antagonist, an adhesion molecule antagonist (e.g., intercellular adhesion molecule (ICAM)-1, ICAM-2, ICAM-3, platelet endothelial adhesion molecule (PCAM), vascular cell adhesion molecule (VCAM)), a leukocyte adhesion-inducing cytokine or growth factor antagonist (e.g., tumor necrosis factor-α (TNF-α), interleukin-1β (IL-1β), monocyte chemotactic protein-1 (MCP-1), or a vascular endothelial growth factor (VEGF)). In some embodiments, a vascular endothelial growth factor (VEGF) inhibitor is administered with one of the microneedles described herein. In some embodiments, two drugs are delivered by the methods described herein. The compounds may be administered in one formulation, or administered serially, in two separate formulations. For example, both a VEGF inhibitor and VEGF are provided. In some embodiments, the VEGF inhibitor is an antibody, for example a humanized monoclonal antibody. In further embodiments, the VEGF antibody is bevacizumab. In another embodiment, the VEGF inhibitor is ranibizumab, aflibercept or pegaptanib. In still other embodiments, the devices and methods described herein can be used to deliver one or more of the following VEGF antagonists: AL8326, 2C3 antibody, AT001 antibody, HyBEV, bevacizumab (Avastin), ANG3070, APX003 antibody, APX004 antibody, ponatinib (AP24534), BDM-E, VGX100 antibody (VGX100 CIRCADIAN), VGX200 (c-fos induced growth factor monoclonal antibody), VGX300, COSMIX, DLX903/1008 antibody, ENMD2076, Sutent (sunitinib malate), INDUS815C, R84 antibody, KD019, NM3, allogenic mesenchymal precursor cells combined with an anti-VEGF agent or antibody, MGCD265, MG516, VEGF-Receptor kinase inhibitors, MP0260, NT503, anti-DLL4/VEGF bispecific antibody, PAN90806, Palomid 529, BD0801 antibody, XV615, lucitanib (AL3810, E3810), AMG706 (motesanib diphosphate), AAV2-sFLT01, soluble Fltl receptor, Cediranib (Recentin), AV-951 (Tivozanib, KRN-951), Stivarga (regorafenib), Volasertib (BI6727), CEP11981, KH903, Lenvatinib (E7080), terameprocol (EM1421), ranibizumab (Lucentis), Votrient (pazopanib hydrochloride), PF00337210, PRS050, SPO1 (curcumin), Carboxyamidotriazole orotate, hydroxychloroquine, linifanib (ABT869, RG3635), Iluvien (fluocinolone acetonide), ALG1001, AGN150998, DARPin MP0112, AMG386, ponatinib (AP24534), AVA101, Vargatef (nintedanib), BMS690514, KH902, golvatinib (E7050), Afinitor (everolimus), Dovitinib lactate (TKI258, CHIR258), ORA101, ORA102, Axitinib (Inlyta, AG013736), Plitidepsin (Aplidin), Lenvatinib mesylate, PTC299, aflibercept (Zaltrap, Eylea), pegaptanib sodium (Macugen, LI900015), Visudyne (verteporfin), bucillamine (Rimatil, Lamin, Brimani, Lamit, Boomiq), R3 antibody, AT001/r84 antibody, troponin (BLS0597), EG3306, vatalanib (PTK787), Bmab100, GSK2136773, Anti-VEGFR Alterase, Avila, CEP7055, CLT009, ESBA903, HuMax-VEGF antibody, GW654652, HMPL010, GEM220, HYB676, JNJ17029259, TAK593, XtendVEGF antibody, Nova21012, Nova21013, CP564959, Smart Anti-VEGF antibody, AG028262, AG13958, CVX241, SU14813, PRS055, PG501, PG545, PT1101, TG100948, ICS283, XL647, enzastaurin hydrochloride (LY317615), BC194, quinolines, COT601M06.1, COT604M06.2, MabionVEGF, SIR-Spheres coupled to anti-VEGF or VEGF-R antibody, Apatinib (YN968D1), and AL3818. In addition, delivery of a VEGF inhibitor or VEGF antagonist using the microneedle devices and methods disclosed herein may be combined with one or more agents listed herein or with other agents known in the art.

In some embodiments, one or more components of a system or device disclosed herein are configured to be assembled with one another. For example, the system or device may comprise one or more syringe barrels.

In some embodiments, the system or device may comprise two or more units, such as a first syringe unit comprising: a first syringe barrel; a needle base in the first syringe barrel; and a needle comprising a needle proximal end engaging the needle base and a needle distal end. In some embodiments, the system or device may comprise a second syringe unit configured to engage a distal end of the first syringe unit, comprising: a second syringe barrel; and a floating seal in the second syringe barrel, and when the first and second syringe units are engaged, the floating seal is configured to elastically engage the needle base. In some embodiments, the system or device may comprise a third syringe unit configured to engage a distal end of the second syringe unit, comprising a third syringe barrel enclosing a flowable composition, and the needle base can be configured to advance the needle to place the needle proximal end and/or the needle distal end in the flowable composition. In any of the embodiments herein, the system or device can comprise one or more syringe units, optionally a fourth syringe unit configured to engage a distal end of the third syringe unit.

In some embodiments, the system or device may comprise a first syringe unit comprising: a first syringe barrel; a needle base and a floating seal in the first syringe barrel elastically engaging each other, the needle base being proximal to the floating seal; and a needle comprising a needle proximal end engaging the needle base and a needle distal end, the needle comprising: (i) a needle distal opening, (ii) a needle body opening between the needle proximal end and the needle distal end, the needle body opening being proximal to the needle distal opening, and (iii) a needle body passageway connecting the needle distal opening and the needle body opening. In some embodiments, the system or device may further comprise a second syringe unit configured to engage a distal end of the first syringe unit, comprising a second syringe barrel enclosing a flowable composition, and the needle base can be configured to advance the needle to place the needle proximal end and/or the needle distal end in the flowable composition. In any of the embodiments herein, the device can comprise one or more syringe units, optionally a third syringe unit configured to engage a distal end of the second syringe unit.

In some embodiments, the system or device may comprise a first syringe unit comprising: a first syringe barrel; a needle base in the first syringe barrel; and a needle comprising a needle proximal end engaging the needle base and a needle distal end, the needle comprising: (i) a needle distal opening, (ii) a needle body opening between the needle proximal end and the needle distal end, the needle body opening being proximal to the needle distal opening, and (iii) a needle body passageway connecting the needle distal opening and the needle body opening. In some embodiments, the system or device may further comprise a second syringe unit configured to engage a distal end of the first syringe unit, comprising: a second syringe barrel; a floating seal in the second syringe barrel, and when the first and second syringe units are engaged, the floating seal is configured to elastically engage the needle base; and a flowable composition, and the needle base can be configured to advance the needle to place the needle proximal end and/or the needle distal end in the flowable composition. In any of the embodiments herein, the device can comprise one or more syringe units, optionally a third syringe unit configured to engage a distal end of the second syringe unit.

III. Methods for Medical Penetration

In some embodiments, described herein are methods for medical puncture, for example, in an eye or other organs or tissues.

As shown in FIGS. 1-11B, in some embodiments the present disclosure provides a medical puncturing or penetration device which comprises syringe barrel 1, an actuation unit (e.g., an elastic movement unit for pushing a needle), hollow puncture needle 6, and flowable composition lumen 7.

In some embodiments, syringe barrel 1 comprises a distal closed end and a proximal open end. In some embodiments, syringe barrel 1 can be designed to have two open ends in an axial direction, and sealing of the distal end can be achieved by installing distal seal 8 at the distal opening of syringe barrel 1. In some embodiments, distal seal 8 can be made of a material that can be punctured by hollow puncture needle 6, such as rubber or the like.

In some embodiments, the actuation unit (e.g., elastic movement unit) comprises actuation member (e.g., pressing element) 2 and floating seal 3, where the floating seal 3 sealingly engages an inside wall of the syringe barrel and is configured to move in an axial direction, e.g., toward the distal end or the proximal end of the syringe barrel. In some embodiments, actuation member (e.g., pressing element) 2 or a portion thereof is located outside the proximal opening of the syringe barrel, so that an operator can press on the actuation member (e.g., pressing element) or portion thereof manually. In some embodiments, floating seal 3 elastically engages actuation member 2, and when pressure is applied on actuation member 2, floating seal 3 can move forward or backward relative to the actuation member (e.g., pressing element). In some embodiments, floating seal 3 is configured to move toward the distal end of the syringe barrel. In some embodiments, floating seal 3 is configured to move toward the proximal end of the syringe barrel. In some embodiments, the position of the actuation member (e.g., pressing element) relative to the syringe barrel is kept still, floating seal 3 is configured to move forward (e.g., in a distal direction) under elastic resilience due to the elastic engagement with the actuation member (e.g., pressing element).

In some embodiments, hollow puncture needle 6 is fixedly connected to actuation member 2. When no pressure is applied to actuation member 2, hollow puncture needle 6 remains proximal to floating seal 3 and the two do not come into contact. In some embodiments, hollow puncture needle 6 itself comprises needle distal opening 6a and needle body opening 6b. In some embodiments, needle distal opening 6a and needle body opening 6b are connected through a needle cavity or needle body passageway of hollow puncture needle 6.

In some embodiments, flowable composition lumen 7 is used for storage, e.g., of a medication and other flowable composition such as a liquid or a gel. In some embodiments, the flowable composition lumen is enclosed by a distal closed end of the syringe barrel, a lumen wall of the syringe barrel, and floating seal 3; that is, the flowable composition lumen occupies a distal portion of a syringe barrel lumen. In some embodiments, since floating seal 3 can move along in an axial direction, flowable composition lumen 7 is configured to have a variable volume, thus the fluid pressure inside flowable composition lumen 7 can change due to an axial movement of floating seal 3.

In some embodiments, using a medical puncturing device disclosed herein comprises applying pressure on actuation member 2, thereby advancing hollow puncture needle 6 forward in a distal direction, sequentially through floating seal 3 (e.g., by puncturing the floating seal or forcing open an existing aperture or slit through the floating seal) and through a distal closed end (e.g., by puncturing the distal closed end or forcing open an existing aperture or slit through the distal closed end) of the syringe barrel. The existing aperture or slit may be through the floating seal, e.g., from a proximal surface of the floating seal to a distal surface of the floating seal, thereby providing a through hole in the floating seal. The existing aperture or slit may be not through the entire floating seal, and advancing the needle distal end through the floating seal may comprise advancement through the existing aperture or slit and puncturing a portion of the floating seal in any suitable combination. For instance, the needle distal end may first advance through an existing aperture or slit from a proximal surface and then puncture the floating seal before emerging from a distal surface of the floating seal, or vice versa. In some embodiments, hollow puncture needle 6 pierces into an apparent or potential tissue void, cavity, or vessel, thereby placing needle distal opening 6a in the apparent or potential tissue void, cavity, or vessel. In some embodiments, needle body opening 6b is positioned inside flowable composition lumen 7, and floating seal 3 is elastically engaged with actuation member 2. In some embodiments, the fluid pressure in flowable composition lumen 7 is higher than the pressure inside the apparent or potential tissue void, cavity, or vessel.

At this time, the flowable composition inside flowable composition lumen 7 can flow through needle body opening 6b and needle distal opening 6a and into the apparent or potential tissue void, cavity, or vessel. In some embodiments, during an injection process, a user can simply maintain the pressure on actuation member 2, e.g., without further increasing the pressure. Under the action of the elastic engagement between floating seal 3 and actuation member 2, the flowable composition (e.g., a solution, a suspension, or a gel) inside flowable composition lumen 7 can enter needle body opening 6b and through the needle body passageway, thus achieving injection, penetration, and/or expansion of the apparent or potential tissue void, cavity, or vessel.

In some embodiments, before hollow puncture needle 6 pierces into an apparent or potential tissue void, cavity, or vessel, external pressure on needle distal opening 6a is higher than the fluid pressure in flowable composition lumen 7, e.g., due to the needle distal opening being in a tissue denser, harder, and/or less deformable than the apparent or potential tissue void, cavity, or vessel. Thus, the flowable composition inside the flowable composition lumen cannot exist needle distal opening 6a and into the surrounding tissue. Take the puncture process of the SCS of the eye as an example, when hollow puncture needle 6 has already pierced sclera 13 but has not yet pierced SCS 14, regardless of whether needle body opening 6b is in fluid communication with flowable composition lumen 7 or not, the flowable composition would not exit from needle distal opening 6a. This is because sclera 13 is relatively dense, and when needle distal opening 6a is inside sclera 13, a relatively high external pressure is applied on needle distal opening 6a. The external pressure is higher than the fluid pressure in flowable composition lumen 7, and the dense tissue such as the sclera essentially functions as a plug that prevents the flowable composition from flowing out.

In some embodiments, by observing whether floating seal 3 moves forward due to the elastic engagement when actuation member 2 is held still under pressure, an operator can determine whether hollow puncture needle 6 has already pierced into an apparent or potential tissue void, cavity, or vessel, thereby informing the operator of the current needle depth and/or location of the needle distal opening and ensure accurate needle placement. In some embodiments, since the injection is controlled by fluid pressure changes in flowable composition lumen 7, the injection process does not require manually applying a force that is transmitted via relatively rigid medium (e.g., solid or liquid) in order to advance and precisely place the needle tip into an apparent or potential tissue void, cavity, or vessel. Rather, an abrupt force applied to actuation member 2 can be buffered due to the elastic engagement between actuation member 2 and floating seal 3, thus allowing more controllable and steady movement of the floating seal. In some embodiments, using a device disclosed herein, fluctuations in the flow speed can be prevented or reduced and steady injection can be achieved.

It should be noted that, the apparent or potential tissue gaps, voids, cavities, cavity systems, or vessels of the present disclosure can include but are not limited to an SCS, an epidural space, a pleural cavity, a peritoneal cavity, an artery, a vein, a joint space (e.g., a knee join space), etc. Thus, the medical puncturing device disclosed herein also has the advantage of being highly versatile for use in any suitable apparent or potential tissue gaps, voids, cavities, cavity systems, or vessels. In some embodiments, the medical puncturing device can be used for SCS puncture and drug delivery, epidural puncture and drug delivery, pleural puncture and intrapleural drug delivery, peritoneal puncture and intraperitoneal drug delivery, or intraarticular injection. For example, applications include accessing suprachoroidal space (ocular), performing epidural injections (spinal cord access), accessing large vessels (arteries/veins) for inserting surgical wires (e.g., to access heart through vessels), accessing vessels for fistula access or catheter insertion, inserting through heart wall without damaging inner wall, accessing the abdomen (e.g. trocar access for minimally invasive surgery), injecting in fat under the skin, accessing insides of amniotic sac without damaging the fetus, performing a knee sac injection without damaging cartilage, injecting inside meninges without damaging brain tissue (drill in skull then use autostop on meninges), injecting between pericardium and heart, injecting between fascia and kidney, injecting between fibrous tissue layer and implants (for e.g. breast implant), injecting into other ocular spaces (e.g., for Deep Anterior Lamellar Keratoplasty (DALK) to separate epithelial cell layer from collagenous layer), or accessing collapsed lungs from outside. Also, the system may be used to deliver gene therapy including but not limited to viral vectors and/or transfected cells. In some embodiments, the flowable composition may include a variety of therapeutics. As non-limiting examples, therapeutics may include mRNA, CRISPR agents, RNAi, antibodies, nanobodies, nanoparticles, proteins, peptides, small molecules, aptamers, cells, extracellular vesicles, microRNA and the like.

In some embodiments, when hollow puncture needle 6 pierces through the syringe barrel distal closed end, the medical puncturing device can be in at least three states: a pre-puncture state, a surface tissue puncture state, and a fluidic communication state.

In some embodiments, in the pre-puncture state, the length range of hollow puncture needle 6 extending from the syringe barrel distal closed end is a pre-puncture length range. Within this range, hollow puncture needle 6 has not yet started puncturing an organism or a tissue thereof.

In some embodiments, a system or device of the present disclosure comprises a flowable composition lumen pre-filled with a flowable composition. In some embodiments, prior to use of the system or device, the needle is already through the floating seal. In some embodiments, prior to use of the system or device, the needle is already through the floating seal and the syringe barrel distal end, e.g., a distal seal sealing the syringe barrel distal end.

In some embodiments, the flowable composition is of a relatively high viscosity, e.g., higher than water-like consistency, such as a gel or paste-like material. Elastic sleeve or sheath 4 shown in the figures of the present disclosure is optional, especially when the viscosity of the flowable composition is sufficient to prevent discharge from the needle body opening and/or needle distal opening when the openings are in the flowable composition lumen. For example, as shown in FIG. 3A, the needle can be through the floating seal such that needle body opening 6b is proximal to the floating seal while needle distal opening 6a is in the flowable composition lumen. Discharge of the flowable composition from the needle body opening can be prevented due to viscosity of the composition, and the elastic sheath is optional. Alternatively, as shown in FIG. 3B, the needle body opening 6b can be in the flowable composition lumen while needle distal opening 6a is outside the flowable composition lumen. Discharge of the flowable composition from the needle distal opening can be prevented due to viscosity of the composition, until the needle distal opening reaches a target tissue, such as an apparent or potential tissue void, cavity, or vessel.

In some embodiments, for example prior to or during the use of the system or device, needle distal opening 6a can be outside the flowable composition lumen, while needle body opening 6b can be proximal to the floating seal (e.g., as shown in FIG. 3C, 6b1) or within the floating seal (e.g., as shown in FIG. 3C, 6b2). Discharge of the flowable composition from the needle distal opening can be prevented due to viscosity of the composition, until the needle distal opening reaches a target tissue, such as an apparent or potential tissue void, cavity, or vessel.

In some embodiments, for example prior to or during the use of the system or device, needle distal opening 6a can be within a distal seal at the syringe barrel distal closed end (e.g., the needle distal opening can be blocked by the distal seal), while needle body opening 6b can be proximal to the floating seal (e.g., as shown in FIG. 3D, 6b1), within the floating seal (e.g., as shown in FIG. 3D, 6b2), or within the flowable composition lumen (e.g., as shown in FIG. 3D, 6b3). Discharge of the flowable composition from the needle distal opening and the needle body opening can be prevented.

In some embodiments, for example prior to or during the use of the system or device, needle distal opening 6a can be within the flowable composition lumen, while needle body opening 6b can be within the floating seal (e.g., as shown in FIG. 3E, 6b1) or within the flowable composition lumen (e.g., as shown in FIG. 3E, 6b2). Discharge of the flowable composition from the needle body opening can be prevented.

In some embodiments, for example prior to or during the use of the system or device, needle distal opening 6a can be within the floating seal, while needle body opening 6b can be proximal to the floating seal (e.g., as shown in FIG. 3F, 6b). Discharge of the flowable composition from the needle body opening can be prevented.

In some embodiments, in the surface tissue puncture state, the length range of hollow puncture needle 6 extending from the syringe barrel distal closed end is a surface tissue puncture length range. Within this range, the distal end of hollow puncture needle 6 has entered a surface tissue (for example, pierced into sclera 13) but has not yet entered the apparent or potential tissue void, cavity, or vessel (for example, not pierced into SCS 14). In some embodiments, because the surface tissue is relatively dense, external pressure on needle distal opening 6a is higher than the fluid pressure in flowable composition lumen 7, therefore, no matter whether needle body opening 6b is connected to flowable composition lumen 7 or not, the flowable composition does not enter needle body opening 6b and/or exit needle distal opening 6a.

In some embodiments, while in the fluidic communication state, the length range of hollow puncture needle 6 extending from the syringe barrel distal closed end is the a fluidic communication. Within this range, the distal end of hollow puncture needle 6 has pierced into the apparent or potential tissue void, cavity, or vessel. In some embodiments, the device can be designed such that in the fluidic communication state, the fluid pressure in flowable composition lumen 7 is higher than the pressure inside the apparent or potential tissue void, cavity, or vessel. In some embodiments, in the fluidic communication state, needle body opening 6b has already positioned inside flowable composition lumen 7, and due to a difference in the internal (e.g., in the apparent or potential tissue void, cavity, or vessel) and external (e.g., in flowable composition lumen 7) pressures, the flowable composition inside lumen 7 can flow into the apparent or potential tissue void, cavity, or vessel through needle body opening 6b, the needle body passageway, and then needle distal opening 6a.

Figure 4A:
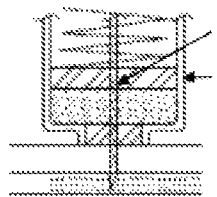
FIGS. 4A-4C are partial structure diagrams of exemplary medical puncturing devices comprising floating seal 3 and needle body opening 6b.
Figure 4B:
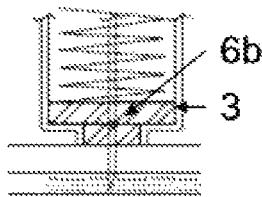

In some embodiments, floating seal 3 moves distally due to the elastic engagement with actuation member 2 (e.g., due to the pressure in the flowable composition lumen being higher than a backpressure at the needle distal opening in the apparent or potential tissue void, cavity, or vessel) until the floating seal seals needle body opening 6b (e.g., as shown in FIGS. 4A-4B). In some embodiments, the axial dimension of the needle body opening is no greater than the thickness of the floating seal. In some embodiments, the needle body opening can be completely sealed or blocked by the floating seal, at which time no more flowable composition exits needle distal opening 6a to enter the tissue void. In some embodiments, when the floating seal blocks the needle body opening, only a portion of the total volume of flowable composition has exited needle distal opening 6a (e.g., as shown in FIG. 4A). In some embodiments, when the floating seal blocks the needle body opening, the total volume of flowable composition in the lumen has exited needle distal opening 6a (e.g., as shown in FIG. 4B).

Figure 4C:
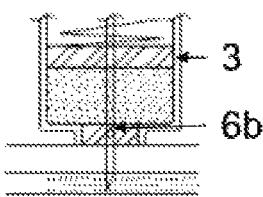

In some embodiments, when the needle body opening can be in the distal seal or in a tissue of a subject, the flowable composition will stop existing needle distal opening 6a (e.g., as shown in FIG. 4C). In some embodiments, the distance between needle distal opening 6a and needle body opening 6b can be keep constant. In some embodiments, the distance between needle distal opening 6a and needle body opening 6b can be varied. For example, a needle having a suitable distance between needle distal opening 6a and needle body opening 6b can be selected based on a known or estimated depth of the tissue to be accessed. In some embodiments, stopper 1a is provided inside the syringe lumen and can be used to limit the forward movement of floating seal 3 in order to achieve precise injection, for example, injection of a pre-determined volume.

In some embodiments, once floating seal 3 contacts stopper 1a, further distal movement of the floating seal is limited, thereby stabilizing floating seal 3 for subsequent operation, for example, as shown in FIGS. 6-11B.

Figure 5A:
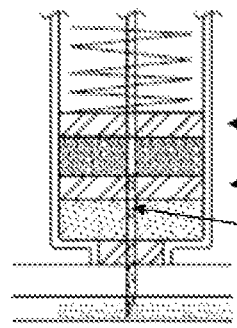
FIGS. 5A-5F are partial structure diagrams of exemplary medical puncturing devices comprising floating seals 3a and 3b and one or more needle body openings (6b or 6b1 and/or 6b2).

In some embodiments, a system or device disclosed herein comprises two or more floating seals. For example, as shown in FIG. 5A, a first lumen is formed between floating seal 3b and the distal seal of the syringe barrel, and a second lumen is formed between floating seal 3a and floating seal 3b. In some embodiments, the first lumen and the second lumen comprise the same flowable material. In some embodiments, the first lumen and the second lumen comprise different flowable compositions. In some embodiments, the first lumen and the second lumen comprise the same medicament (e.g., active pharmaceutical ingredient) in the same or different flowable carriers or excipients. In some embodiments, the first lumen and the second lumen comprise different medicaments (e.g., active pharmaceutical ingredients) in the same or different flowable carriers or excipients. In some embodiments, the first lumen comprises a medicament and the second lumen comprises a pharmaceutically acceptable carrier or excipient such as a saline, or vice versa.

Figure 5B:
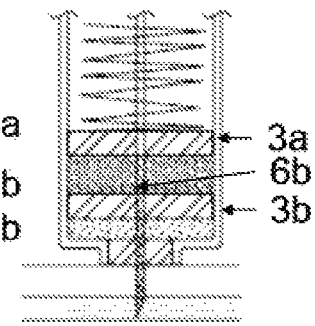
Figure 5C:
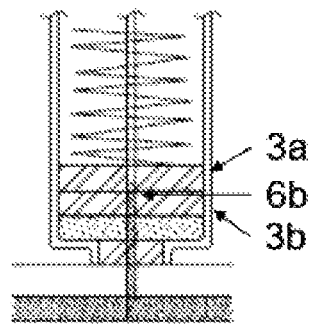

In some embodiments, the flowable compositions in the first lumen and the second lumen can be sequentially delivered to an apparent or potential tissue void, cavity, or vessel. In some embodiments, the flowable compositions in the first lumen and the second lumen can be mixed in the apparent or potential tissue void, cavity, or vessel. In some embodiments, the flowable composition in the first lumen enters the apparent or potential tissue void, cavity, or vessel in order to access and/or expand the tissue void, cavity, or vessel. Subsequently, the flowable composition in the second lumen comprising a medicament can enter the apparent or potential tissue void, cavity, or vessel. For example, as shown in FIG. 5A, when needle distal opening 6a is in the apparent or potential tissue void, cavity, or vessel while needle body opening 6b is in the first lumen (between floating seal 3b and the distal seal of the syringe barrel), the flowable composition in the first lumen is delivered to the tissue. In FIG. 5B, needle distal opening 6a can be held still in the apparent or potential tissue void, cavity, or vessel, when floating seal 3b moves distally and needle body opening 6b contacts the second lumen (between floating seal 3a and floating seal 3b). This way, the flowable composition in the second lumen starts to be delivered to the tissue until a volume is delivered and/or floating seal 3a (or floating seal 3a and floating seal 3b together) blocks needle body opening 6b, as shown in FIG. 5C. In some embodiments, a set (e.g., predetermined) volume of the flowable composition in the first lumen and/or a set (e.g., predetermined) volume of the flowable composition in the second lumen can be delivered to the apparent or potential tissue void, cavity, or vessel. In some embodiments, the dimension of needle body opening 6b along the needle axis is greater than the thickness of floating seal 3b such that a first flowable composition (between floating seal 3b and the distal seal of the syringe barrel) and a second flowable composition (between floating seal 3b and floating seal 3a) can be sequentially and continuously delivered to the apparent or potential tissue void, cavity, or vessel through the needle distal opening. In some embodiments, the dimension of needle body opening 6b along the needle axis is no greater than the thickness of floating seal 3a and floating seal 3b combined. In some embodiments, the dimension of needle body opening 6b along the needle axis is greater than the thickness of floating seal 3b and less than the thickness of floating seal 3a and floating seal 3b combined. In some embodiments, a system or device disclosed herein comprises one or more additional floating seals (e.g., a third floating seal, 3c) that are proximal to floating seal 3a, distal to floating seal 3b, and/or between floating seal 3a and floating seal 3b, such that a third flowable composition may be delivered before the first flowable composition, after the second flowable composition, or between the first and second flowable compositions.

Figure 5D:
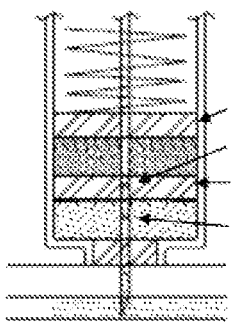
Figure 5E:
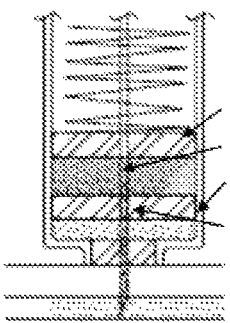
Figure 5F:
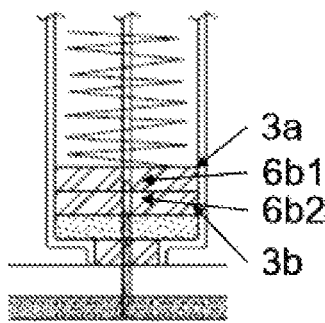

In some embodiments, a system or device disclosed herein comprises two or more needle body openings. In some embodiments, a system or device disclosed herein comprises two or more needle body openings and two or more floating seals. For example, as shown in FIG. 5D, when needle distal opening 6a is in the apparent or potential tissue void, cavity, or vessel while needle body opening 6b1 is in the first lumen (between floating seal 3b and the distal seal of the syringe barrel) and needle body opening 6b2 is blocked by floating seal 3b, the flowable composition in the first lumen is delivered to the tissue. In FIG. 5E, needle distal opening 6a can be held still in the apparent or potential tissue void, cavity, or vessel, when floating seal 3b moves distally to block needle body opening 6b1, allowing needle body opening 6b2 to contact the second lumen (between floating seal 3a and floating seal 3b). This way, the flowable composition in the second lumen starts to be delivered to the tissue until a volume is delivered and/or floating seal 3a (or floating seal 3a and floating seal 3b together) blocks needle body opening 6b2 (and/or needle body opening 6b1) as shown in FIG. 5F. In some embodiments, a set (e.g., predetermined) volume of the flowable composition in the first lumen and/or a set (e.g., predetermined) volume of the flowable composition in the second lumen can be delivered to the apparent or potential tissue void, cavity, or vessel. In some embodiments, the distance between needle body opening 6b1 and needle body opening 6b2 along the needle axis is greater than the thickness of floating seal 3b such that a first flowable composition (between floating seal 3b and the distal seal of the syringe barrel) and a second flowable composition (between floating seal 3b and floating seal 3a) can be sequentially and continuously delivered to the apparent or potential tissue void, cavity, or vessel through the needle distal opening. In some embodiments, the distance between needle body opening 6b1 and needle body opening 6b2 along the needle axis is no greater than the thickness of floating seal 3a and floating seal 3b combined. In some embodiments, the distance between needle body opening 6b1 and needle body opening 6b2 along the needle axis is greater than the thickness of floating seal 3b and less than the thickness of floating seal 3a and floating seal 3b combined. In some embodiments, a system or device disclosed herein comprises one or more additional needle body openings (e.g., a third needle body opening, 6b3) that are proximal to needle body opening 6b2, distal to needle body opening 6b1, and/or between needle body openings 6b1 and 6b2, such that a third flowable composition may be delivered before the first flowable composition, after the second flowable composition, or between the first and second flowable compositions.

Described below are multiple embodiments to control the termination of the injection process using a medical puncturing device disclosed herein.

In some embodiments, when the medical puncturing device is in a fluidic communication state, floating seal 3 moves forward due to the elastic engagement with actuation member 2 until it seals needle body opening 6b. Once needle body opening 6b is sealed, the injection process is terminated. In some embodiments, the axial position of needle body opening 6b within the flowable composition lumen 7 limits the maximum injection volume of the medical puncturing device. In some embodiments, when needle body opening 6b is blocked or sealed by floating seal 3, floating seal 3 has not contacted a wall at the syringe barrel distal closed end. In some embodiments, flowable composition lumen 7 is not completely emptied and there is still flowable composition between floating seal 3 and the wall at the syringe barrel distal closed end.

In some embodiments, when flowable composition lumen 7 needs to be emptied, floating seal 3 can be designed to seal needle body opening 6b when the floating seal contacts the syringe barrel distal closed end. In some embodiments, needle body opening 6b is at the distal end of flowable composition lumen 7. In some embodiments, floating seal 3 contacts a wall at the syringe barrel distal closed end and needle body opening 6b is blocked or sealed by floating seal 3 and/or the wall at the syringe barrel distal closed end. In some embodiments, flowable composition lumen 7 is emptied and there is no or little flowable composition between floating seal 3 and the wall at the syringe barrel distal closed end.

In some embodiments, as the flowable composition inside flowable composition lumen 7 gradually enters the apparent or potential tissue void, cavity, or vessel, there can be a state wherein the fluid pressure inside flowable composition lumen 7 reaches equilibrium with the pressure in the apparent or potential tissue void, cavity, or vessel. At this time, floating seal 3 no longer moves, due to the balance of forces. In order to continue injection and/or empty flowable composition lumen 7, additional force is needed on floating seal 3 in order to move it forward toward the syringe barrel distal closed end.

For example, as shown in FIGS. 2A-2E, one, two, or more axially extending sliding grooves (not shown) can be provided on a body wall of syringe barrel 1. A slider matching a sliding groove can be provided on actuation member 2 (e.g., a slider can comprise a portion of actuation member 2 extending outside of syringe barrel 1), thus increasing the upper limit of the movement distance or stroke of actuation member 2 since the movement is not limited by the proximal end of actuation member 2. When floating seal 3 can no longer move due to the equilibrium of forces (e.g., between pressure inside flowable composition lumen 7 and the apparent or potential tissue void, cavity, or vessel), more pressure can be applied on a slider of actuation member 2 to drive actuation member 2 forward distally, which in turn can increase the elastic resilience between floating seal 3 and actuation member 2, thus breaking the force equilibrium and moving floating seal 3 forward toward the distal end of the syringe barrel. This way, more flowable composition can be expelled from flowable composition lumen 7, in some embodiments emptying flowable composition lumen 7.

In some embodiments, other drive structures can be used to move floating seal 3 further until it contacts a wall of the syringe barrel distal closed end. Exemplary drive structures are described below.

In some embodiments, an axially extending sliding groove can be provided on a peripheral wall of syringe barrel 1, proximal to floating sealing 3. In some embodiments, a manual control part can include an actuation member 2' (which may be in the form of a slider) that is slidingly matched with the sliding groove of the peripheral wall of the syringe barrel. In some embodiments, a portion of actuation member (e.g., slider) 2' extends outside of the syringe barrel through the sliding groove, which is convenient for a user to manipulate. In some embodiments, floating sealing 3 and actuation member (e.g., slider) 2' form an elastic connection. For example, floating sealing 3 and actuation member (e.g., slider) 2' can engage each other via elastic piece (e.g., spring) 4' as shown in Step 1, FIG. 2G, whereas floating sealing 3 and actuation member (e.g., slider) 2 can engage each other via elastic piece (e.g., spring) 4. In some embodiments, actuation member 2 may comprise a rod that is configured to insert through a space between portions of actuation member 2' such that actuation members 2 and 2' do not interfere with each other. In some embodiments, elastic piece (e.g., spring) 4 and elastic piece (e.g., spring) 4' may function independently and do not interfere with each other. In some embodiments, spring 4 is smaller than spring 4', for instance, the average diameter of spring 4 can be can be smaller than the average diameter of spring 4'. In some embodiments, elastic piece 4' is nested inside elastic piece 4. In Step 2, FIG. 2G, a force can be applied to actuation member 2 to move the needle distally while maintaining the position of floating sealing 3. In some embodiments, as shown in Step 3, FIG. 2G, a force can be applied on actuation member 2' to move it distally along the axial direction of the sliding groove on the peripheral wall of the syringe barrel. This way, elastic piece (e.g., spring) 4' between floating sealing 3 and actuation member (e.g., slider) 2' can be elastically compressed. In some embodiments, when the position of actuation member (e.g., slider) 2' is maintained, under the action of an elastic force, floating sealing 3 can break the equilibrium of forces and continue to move distally until the volume of discharged flowable composition reaches a target volume. In some embodiments, actuation member (e.g., slider) 2' can be moved distally as shown in Step 4, FIG. 2G, to move floating sealing 3 further distally in order to discharge the flowable composition from the needle.

In some embodiments, the medical puncturing device comprises an element configured for an operator to manually control movement of the floating seal using one or both hands. In some embodiment, the manual control element can be moved using one or more fingers, for example, one finger of the same hand holding the syringe barrel. In some embodiments, the manual control element is fixed to floating seal 3 and partially extends outside the syringe barrel. In some embodiments, when the flowable composition volume injected into the apparent or potential tissue void, cavity, or vessel does not reach a target volume, while floating seal 3 is no longer moving due to the equilibrium of forces, the operator can drive further movement of floating seal 3 forward by moving the portion of the manual control element that extends outside the syringe barrel, until the expelled flowable composition volume reaches the target volume. In some embodiments, using the manual control element helps empty flowable composition lumen 7. These embodiments are not limited to situations where flowable composition lumen 7 needs to be emptied.

In some embodiments, the medical puncturing device can achieve delivery (e.g., via injection) of a flowable composition of a defined volume with precision, and/or the ability to control the volume to be delivered. In some embodiments, the defined volume is a preset volume prior to the delivery. In some embodiments, the defined volume is one of multiple volumes that an operator can select during the delivery, and the delivered volume may be different from a preset volume. In some embodiments, as shown in FIGS. 1A-1F, FIGS. 2A-2F, and FIG. 11, axial stopper 1a is provided inside the syringe lumen and distal to floating seal 3, and is used to limit the forward movement of floating seal 3. In some embodiments, when the medical puncturing device is in the fluidic communication state, needle body opening 6b can be distal to axial stopper 1a, and floating seal 3 can move forward due to the elastic engagement with actuation member 2.

In some embodiments, floating seal 3 is moved to the position limited by axial stopper 1*a*. In some embodiments, when floating seal 3 moves to the position limited by axial stopper 1*a*, pressure in flowable composition lumen 7 is still no less than the pressure inside the apparent or potential tissue void, cavity, or vessel. In some embodiments, floating seal 3 can be pushed forward to the position limited by axial stopper 1*a* by the elastic resilience between floating seal 3 and actuation member 2, and there is no need to rely on additional driving structure or force to move floating seal 3 to the position limited by axial stopper 1*a*.

In some embodiments, before floating seal 3 is moved to the position limited by axial stopper 1*a* by the elastic resilience between the floating seal and actuation member 2, pressure in flowable composition lumen 7 has already become equal with the pressure inside the apparent or potential tissue void, cavity, or vessel (that is, due to balance of forces, floating seal 3 is no longer moving before it reaches axial stopper 1*a*). At this time, just by the elastic resilience between floating seal 3 and actuation member 2, floating seal 3 is not pushed forward to the position limited by axial stopper 1*a*. Thus, in some embodiments, one or more additional driving structure or mechanism can be employed to further push forward floating seal 3. For example, the additional driving structure or mechanism can comprise a manual control element described herein (e.g., as shown in FIGS. 2A-2E). In some embodiments, axial stopper 1*a* provides a mechanism for achieving fluid injection of set volumes.

Described below are multiple embodiments for puncture and injection timing of a medical puncturing device disclosed herein.

In some embodiments, when the medical puncturing device is in pre-puncture state, that is, when the length of hollow puncture needle 6 extending from the syringe barrel distal closed end is within the pre-puncture length range (or when hollow puncture needle 6 has already pierced the syringe barrel distal closed end but has not yet started puncturing the organism or a tissue thereof), needle body opening 6*b* remains above (e.g., proximal to) flowable composition lumen 7. When provided in this way, early leakage from needle distal opening 6*a* can be prevented and the reliability of the medical puncturing device can be improved.

In some embodiments, corresponding structure(s) can be provided on the device to prevent early leakage before hollow puncture needle 6 punctures the tissue and/or before needle distal opening 6*a* reaches the apparent or potential tissue void, cavity, or vessel. For example, axially extending circular contacting element 1*b* can be formed at the syringe barrel distal closed end. In some embodiments, the axial length of circular contacting element 1*b* is set to be the same as the difference between the upper and lower limits of the pre-puncture length range of hollow puncture needle 6 (that is, the difference in needle pre-puncture lengths between when hollow puncture needle 6 pierces the syringe barrel distal closed end and when it starts puncturing the organism or tissue). Under this setting, as long as the distal end of hollow puncture needle 6 is still within the axial length range of circular contacting element 1*b*, early leakage will not happen at needle distal opening 6*a*. When puncturing, circular contacting element 1*b* can come into contact with the surface of the organism or tissue first to stabilize the medical puncturing device. Then, pressure can be applied to actuation member 2 to start the puncture operation.

In some embodiments, when the medical puncturing device is in the surface tissue puncture state, that is, when the length of hollow puncture needle 6 extending from the syringe barrel distal closed end is within the surface tissue puncture length range (or when the distal end of hollow puncture needle 6 has pierced the surface tissue but has not yet entered the apparent or potential tissue void, cavity, or vessel), needle body opening 6*b* is at least partially connected to flowable composition lumen 7. In some embodiments, before the distal end of hollow puncture needle 6 pierces into the apparent or potential tissue void, cavity, or vessel, fluidic communication among flowable composition lumen 7, needle distal opening 6*a* and needle body opening 6*b* is established. In some embodiments, the flowable composition in lumen 7 can enter the needle body passageway (via needle body opening 6*b*) of hollow puncture needle 6 in advance, removing at least part of the air that may be in the needle body passageway, thereby reducing the amount of air entering the apparent or potential tissue void, cavity, or vessel.

In some embodiments, when the distal end of hollow puncture needle 6 starts to pierce into the surface tissue, needle body opening 6*b* starts to connect with flowable composition lumen 7. In some embodiments, when the distal end of hollow puncture needle 6 pierces into the apparent or potential tissue void, cavity, or vessel, the needle body passageway of hollow puncture needle 6 has already been filled with the flowable composition, thereby eliminating or reducing the possibility of air entering the apparent or potential tissue void, cavity, or vessel.

In some embodiments, when the medical puncturing device is in the fluidic communication state, that is, when the length of hollow puncture needle 6 extending from the syringe barrel distal closed end is within the fluidic communication length range (or when the distal end of hollow puncture needle 6 has pierced into the apparent or potential tissue void, cavity, or vessel), needle body opening 6*b* has been positioned inside flowable composition lumen 7, achieving maximum flow at needle body opening 6*b* and thereby increasing injection speed.

The embodiments described herein can be implemented separately or in any suitable combination.

In some embodiments, a device disclosed herein can prevent fluid backflow and/or reverse spill through needle body opening 6*b*.

In some embodiments, there is a risk for fluid backflow and/or reverse spill from needle body opening 6*b* when needle distal opening 6*a* is connected with flowable composition lumen 7, while needle body opening 6*b* is still at the proximal end of floating seal 3. In some embodiments, there is a risk for fluid backflow and/or reverse spill from needle body opening 6*b* when needle distal opening 6*a* is inside the apparent or potential tissue void, cavity, or vessel, while needle body opening 6*b* is still at the proximal end of floating seal 3. In some embodiments, an elastic sheath 4 covering the outside of hollow puncture needle 6 can be provided within the actuation unit (e.g., elastic movement unit), e.g., between the needle base and floating seal 3. In some embodiments, when needle body opening 6*b* is at the proximal end of floating seal 3 (e.g., when needle body opening 6*b* is not connected to flowable composition lumen 7), elastic sheath 4 can keep the needle body opening 6*b* sealed, thereby effectively avoiding backflow and/or reverse spill of the flowable composition, preventing contamination of the area proximal to floating seal 3, reducing fluid loss, and improving product reliability.

In some embodiments, elastic sheath 4 is not used to seal needle body opening 6*b*, but simply as an elastic engagement part between floating seal 3 and actuation member 2.

In some embodiments, by moving actuation member 2 forward, elastic sheath 4 between floating seal 3 and actuation member 2 can become compressed, thereby forming elastic resilience between floating seal 3 and actuation member 2, which can in turn drive floating seal 3 forward. In some embodiments, the elastic engagement part between floating seal 3 and actuation member 2 can comprise or be a spring 5, which is attached to floating seal 3 and actuation member 2 at its two axial ends, respectively. The attachment at either or both ends of the spring can be direct or indirect. The attachment at either or both ends of the spring can be releasable or not releasable. The spring, the floating seal, and the actuation member (e.g., pressing element) can be separately manufactured and then assembled in any suitable order. Alternatively, any two or more of the spring, the floating seal, and the actuation member (e.g., pressing element) can be integral, e.g., made as one piece. Spring 5 and elastic sheath 4 can be implemented separately or in combination.

In some embodiments, the elastic engagement between floating seal 3 and actuation member 2 can be achieved through other methods besides providing one or more elastic engagement parts. For example, floating seal 3 and actuation member 2 can be provided as a one-piece integrated actuation unit (e.g., elastic movement unit).

In some embodiments, provided herein are devices and methods for implantation into apparent or potential tissue gaps, cavity systems, and vessels using a medical puncturing device disclosed herein. For ease of understanding, a catheter is used as an example for the implanted medical device. In some embodiments, a method disclosed herein comprises using a catheter guiding structure for guiding catheter 11 into the needle body passageway of hollow puncture needle 6. In some embodiments, a catheter guiding structure is provided in a medical puncturing device disclosed herein.

Figure 6:
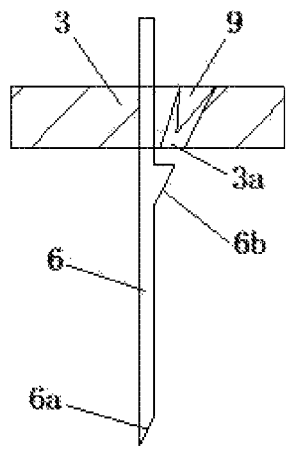
FIG. 6 shows a partial structure diagram of an exemplary medical puncturing device comprising a through angled guiding groove 3a and one-way valve 9.
Figure 7:
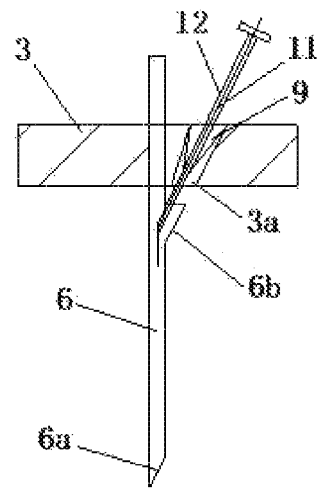
FIG. 7 shows a partial structure diagram of an exemplary medical puncturing device comprising a through angled guiding groove 3a and one-way valve 9.
Figure 8:
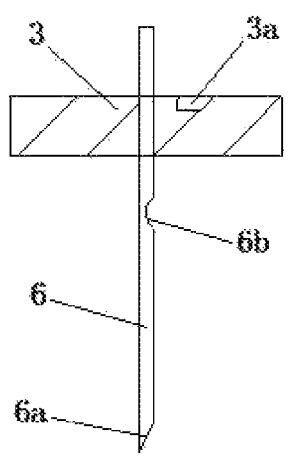

In some embodiments, as shown in FIGS. 6-8, the catheter guiding structure comprises an angled guiding groove 3a, which is provided in or engages floating seal 3 and extends towards hollow puncture needle 6 at an angle. In some embodiments, when flowable composition lumen 7, needle body opening 6b, and needle distal opening 6a are connected, a flowable composition can enter and expand the apparent or potential tissue void, cavity, or vessel. In some embodiments, catheter 11 can be implanted through angled guiding groove 3a, needle body opening 6b, the needle body passageway of hollow puncture needle 6, and needle distal opening 6a into the expanded apparent or potential tissue void, cavity, or vessel.

It should be noted that, angled guiding groove 3a can be provided as a groove through floating seal 3 in a proximal/distal direction, or as a non-through groove formed on a proximal surface of floating seal 3.

In some embodiments, angled guiding groove 3a is a through groove. In some embodiments, the catheter guiding structure further comprises valve 9 provided in or engages angled guiding groove 3a, and the valve may be a one-way valve configured to open and close. In some embodiments, the valve comprises a plurality of leaflets configured to open or close the valve. In some embodiments, in the absence of external force, one-way valve 9 is closed and prevents a flowable composition inside flowable composition lumen 7 from leaking through the valve. In some embodiments, in the presence of an opening force, the plurality of leaflets of the valve can be forced open so that catheter 11 can thread into needle body opening 6b through the opened valve. In some embodiments, the catheter guiding structure further comprises a guiding groove plug configured to be removably inserted in angled guiding groove 3a, and the guiding groove plug can be pulled out when catheter 11 needs to be implanted.

In some embodiments, angled guiding groove 3a is a non-through groove. In some embodiments, the angled guiding groove is punctured directly by catheter 11 to be implanted. In some embodiments, the angled guiding groove is punctured by a piercing component other than the catheter, and catheter 11 can be threaded through the punctured opening into needle body opening 6b.

In some embodiments, to match the guiding direction of angled guiding groove 3a, needle body opening 6b can be provided as an angled opening, which opens obliquely backwards, so that needle body opening 6b can align with angled guiding groove 3a, thereby precisely guiding catheter 11 through the angled guiding groove and into the needle body opening.

Figure 9:
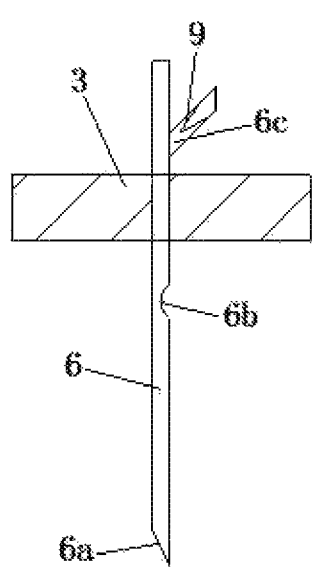
FIG. 9 shows a partial structure diagram of an exemplary medical puncturing device comprising an angled guiding needle hole 6c and one-way valve 9.
Figure 10:
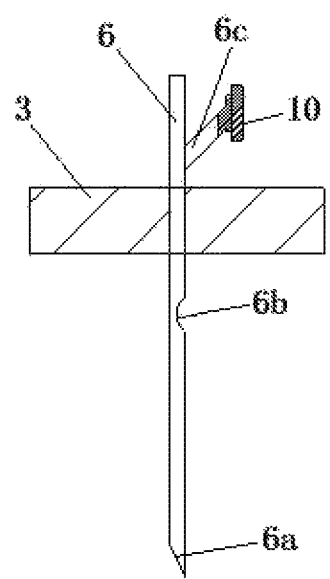
FIG. 10 shows a partial structure diagram of an exemplary medical puncturing device comprising an angled guiding needle hole 6c and needle hole plug 10.
Figure 11A:
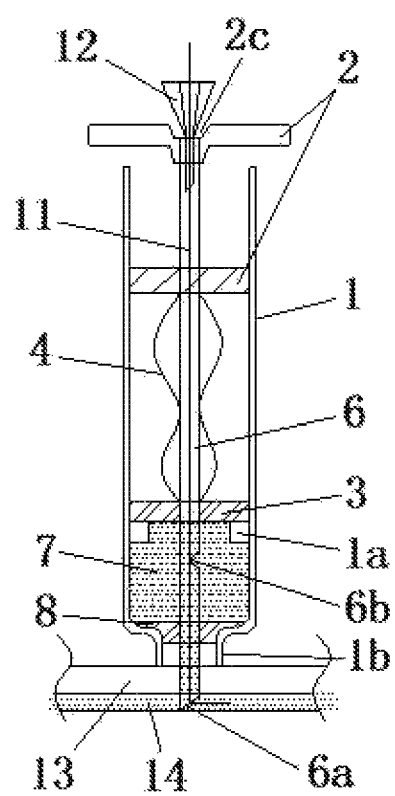
FIGS. 11A-11B show schematic diagrams of implanting catheter 11 into SCS 14 using an exemplary medical apparatus assembly comprising a central guiding groove 2c.
Figure 11B:
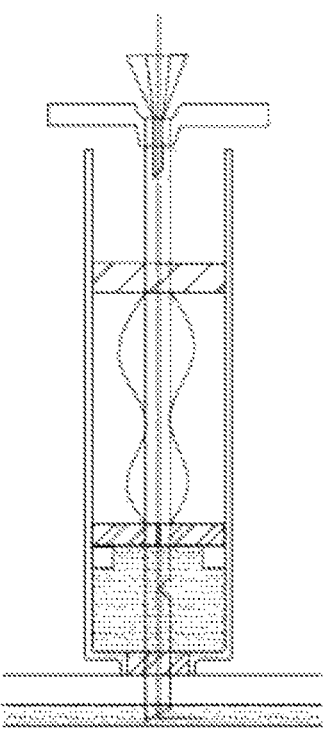

In some embodiments, for example as shown in FIG. 9 and FIG. 10, the catheter guiding structure comprises an angled guiding needle hole 6c which is formed or provided on the body wall of hollow puncture needle 6 and opens obliquely backwards. In some embodiments, angled guiding needle hole 6c remains proximal to floating seal 3, for example, when the medical puncturing device is in a fluidic communication state. In some embodiments, catheter 11 can be threaded into the needle body passageway of hollow puncture needle 6 through angled guiding needle hole 6c. In some embodiments, catheter 11 can be implanted into an apparent or potential tissue void, cavity, or vessel (or an apparent or potential tissue void, cavity, or vessel that has been expanded with a flowable composition) through needle distal opening 6a.

In some embodiments, the catheter guiding structure can further comprise valve 9 provided in or engages angled guiding needle hole 6c, and the valve may be a one-way valve configured to open and close. In some embodiments, the valve comprises a plurality of leaflets configured to open or close the valve. In some embodiments, in the absence of external force, one-way valve 9 is closed and prevents a flowable composition inside flowable composition lumen 7 from leaking through the valve. In some embodiments, in the presence of an opening force, the plurality of leaflets of the valve can be forced open so that catheter 11 can thread into a needle body passageway (which may be connected to or separate from the needle body passageway connecting needle body opening 6b and needle distal opening 6a) through the opened valve and angled guiding needle hole 6c. In some embodiments, the catheter guiding structure can further comprise needle hole plug 10 configured to be removably inserted in angled guiding needle hole 6c, and needle hole plug 10 can be pulled out for the implantation operation of catheter 11 to begin. In some embodiments, guiding needle hole 6c is connected needle distal opening 6a. The needle body passageway connecting needle distal opening 6a and needle body opening 6b can be the same as or separate from the needle body passageway connecting needle distal opening 6a and guiding needle hole 6c. In some embodiments, guiding needle hole 6c is connected to a needle distal opening other than needle distal opening 6a connected to needle body opening 6b. The needle body passageway connecting needle body opening 6b to a needle distal end can be completely separate from the needle body passageway connecting guiding needle hole 6c to a needle distal end. The needle body passageway connecting needle body opening 6b to a needle distal end can be at least partially overlapping or in fluidic communication with the needle body passageway connecting guiding needle hole 6c to a needle distal end.

In some embodiments, for example as shown in FIG. 11, the catheter guiding structure comprises a central guiding groove 2c that is formed or provided on a proximal surface of actuation member 2. In some embodiments, central guiding groove 2c comprises an aperture or can form an aperture in the center of proximal surface of actuation member 2. In some embodiments, central guiding groove 2c can be punctured to provide an aperture. In some embodiments, a needle proximal opening is provided on hollow puncture needle 6 and is aligned with central guiding groove 2c along the axis. In some embodiments, when catheter 11 needs to be implanted, central guiding groove 2c can be punctured and catheter 11 can be threaded into a needle body passageway (which may be connected to or separate from the needle body passageway connecting needle body opening 6b and needle distal opening 6a) through the punctured opening of central guiding groove 2c and the needle proximal opening of hollow puncture needle 6. In some embodiments, catheter 11 can be implanted into an apparent or potential tissue void, cavity, or vessel (or an apparent or potential tissue void, cavity, or vessel that has been expanded with a flowable composition) through a needle distal opening, such as needle distal opening 6a or a different needle distal opening.

In some embodiments, disclosed herein is a kit comprising components configured to be assembled to form a medical puncturing device disclosed herein.

In some embodiments, the kit for assembling a medical puncturing device comprises a puncture control module and a flowable composition storage module (e.g., a fluid storage module). In some embodiments, the puncture control module and the flowable composition storage module are independently manufactured and/or provided. In some embodiments, the puncture control module comprises a first syringe unit, as well as an actuation unit (e.g., elastic movement unit), and hollow puncture needle 6, which are provided inside a syringe barrel of the first syringe unit. It can be seen based on the embodiments disclosed herein that the puncture control module can further comprise other parts or components, such as elastic sheath 4 and spring 5. In some embodiments, the fluid storage module comprises a second syringe unit, flowable composition lumen 7 which is formed inside a syringe barrel of the second syringe unit, and a module packaging component which is removably provided at the proximal end of the second syringe unit. In some embodiments, a removable connection structure is formed between the first syringe unit and the second syringe unit. In some embodiments, the first syringe unit and the second syringe unit form syringe barrel 1 after being connected with each other. It can be seen based on the embodiments disclosed herein that the fluid storage module can further comprise other parts such as distal seal 8.

| In some embodiments, the puncture control module and the fluid storage module can be manufactured, assembled, and/or packaged separately, and then assembled with each other and optionally with other modules, components, and/or parts into the medical puncturing device disclosed herein. In some embodiments, the module packaging component is used to seal the proximal end of flowable composition lumen 7. In some embodiments, when assembling the puncture control module and the fluid storage module, the module packaging component can be removed.

In some embodiments, provided herein is a medical apparatus assembly and a system comprising the same. As shown in FIG. 7 and FIG. 11, in some embodiments the medical apparatus assembly comprises catheter 11 and the medical puncturing device comprising the catheter guiding structure disclosed herein. In some embodiments, catheter 11 can be implanted into an apparent or potential tissue void, cavity, or vessel by the medical puncturing device. The medical apparatus assembly described herein can have all of the technical effects provided by the medical puncturing device.

In some embodiments, the medical apparatus assembly comprises hollow auxiliary guiding needle 12, which is matched to be used with the catheter guiding structure. In some embodiments, the needle body passageway diameter of auxiliary guiding needle 12 is large enough to accommodate catheter 11 and allow the catheter to thread in. In some embodiments, during an operation to implant catheter 11, auxiliary guiding needle 12 is connected to the catheter guiding structure so that catheter 11 can sequentially go through the needle body passageway of auxiliary guiding needle 12, the catheter guiding structure, the needle body passageway of hollow puncture needle 6, and then into an apparent or potential tissue void, cavity, or vessel through needle distal opening 6a. In some embodiment, the apparent or potential tissue void, cavity, or vessel is expanded with a flowable composition using a medical puncturing device disclosed herein, prior to the implant of the catheter. In some embodiment, the catheter is implanted as the apparent or potential tissue void, cavity, or vessel is being expanded with a flowable composition using a medical puncturing device disclosed herein. In some embodiment, the catheter is implanted prior to the apparent or potential tissue void, cavity, or vessel being expanded with a flowable composition using a medical puncturing device disclosed herein.

In some embodiments, as shown in FIG. 7, the catheter guiding structure comprises through angled guiding groove 3a and one-way valve 9, which is embedded in angled guiding groove 3a and can be opened and closed. In some embodiments, needle body opening 6b is provided as an angled opening which opens obliquely backwards. In some embodiments, when implanting catheter 11, auxiliary guiding needle 12 is used to open one-way valve 9 so that the auxiliary guiding needle can be positioned inside angled guiding groove 3a. In some embodiments, the distal end of auxiliary guiding needle 12 advances into needle body opening 6b, and catheter 11 can sequentially advance through the needle body passageway of auxiliary guiding needle 12, the needle body passageway of hollow puncture needle 6, and the needle distal opening 6a and then be implanted into an apparent or potential tissue void, cavity, or vessel.

In some embodiments, as shown in FIG. 11, the catheter guiding structure comprises a central guiding groove 2c. In some embodiments, a needle proximal opening is formed on hollow puncture needle 6, which is aligned with central guiding groove 2c along its axis. In some embodiments, when implanting catheter 11, central guiding groove 2c can be punctured by auxiliary guiding needle 12, such that auxiliary guiding needle 12 is axially aligned with the proximal opening of hollow puncture needle 6. In some embodiments, catheter 11 is threaded into a needle body passageway of hollow puncture needle 6 by sequentially advancing through a needle body passageway of auxiliary guiding needle 12, and a proximal opening of hollow puncture needle 6, and is then implanted into an apparent or potential tissue void, cavity, or vessel through a needle distal opening such as needle distal opening 6a.

In some embodiments, the pressing shaft (e.g., pressing shaft 2 in FIG. 12) comprises a threaded portion configured to be in threaded engagement with the control knob 1 (e.g., control knob 17 in FIG. 12). For example, the control knob can comprises an internal helical thread configured to engage a threaded portion of the pressing shaft. In some embodiments, the control knob can be rotated along a central axis, and through the threaded engagement, rotation of the control knob can drive translation of the pressing shaft in an axial direction. In some embodiments, the pressing shaft is moved along a helical path having a rotatory component and a translational component in an axial direction relative to the housing (or shell) 22. In some embodiments, depending on whether the control knob is rotated clockwise or counterclockwise, the translational movement of the pressing shaft can be in a distal direction (e.g., towards an eye of a subject) or in a proximal direction (e.g., towards an operator). In some examples, clockwise rotation of the control knob advances the pressing shaft in a distal direction, whereas counterclockwise rotation of the control knob retracts the pressing shaft in a proximal direction. In other examples, counterclockwise rotation of the control knob advances the pressing shaft in a distal direction, whereas clockwise rotation of the control knob retracts the pressing shaft in a proximal direction.

In some embodiments, the pressing shaft (e.g., pressing shaft 2 in FIG. 12) is coupled to the syringe needle (e.g., syringe needle 6 in FIG. 12) such that movement of the pressing shaft in an axial direction can lead to and/or allow movement of the syringe needle. In some embodiments, the pressing shaft and the syringe needle are directly coupled. In some embodiments, the pressing shaft and the syringe needle are indirectly coupled. In some embodiments, the pressing shaft and the syringe needle are elastically coupled. In some embodiments, the pressing shaft and the syringe needle elastically engage each other. In some embodiments, the pressing shaft and the syringe needle are coupled via an elastic connection. In some embodiments, the pressing shaft and the syringe needle are fixedly or removably coupled. In some embodiments, the pressing shaft and the syringe needle fixedly or removably engage each other. In some embodiments, the pressing shaft and the syringe needle are coupled via a fixed connection. In some embodiments, the connection between the pressing shaft and the syringe needle is sufficiently rigid such that the pressing shaft can drive advancement or retraction of the syringe needle. In some embodiments, the syringe needle is provided on a needle base or seat that is part of the pressing shaft or that is directly or indirectly coupled to the pressing shaft. In some embodiments, the needle base or seat is elongated axially and has a smaller cross-sectional area than the cross-sectional area of a portion of the pressing shaft that directly abuts the needle base or seat. In some embodiments, the needle base or seat is fixedly coupled to the pressing shaft. In some embodiments, the needle base or seat is integral to the pressing shaft. In some embodiments, the pressing shaft and the syringe needle are coupled via a needle base or seat that is sufficiently rigid in at least an axial direction, such that the pressing shaft can be moved axially distally or proximally in order to advance or retract the syringe needle relative to the housing or shell.

In some embodiments, the pressing shaft (e.g., pressing shaft 2 in FIG. 12) and the piston rod (e.g., push rod 15 in FIG. 12) are coupled via an elastic element or piece, such as a spring (e.g., spring 5 in FIG. 12). In some embodiments, the elastic element or piece is directly or indirectly coupled to the pressing shaft and/or the needle base or seat, or a portion thereof. For example, a portion (e.g., a proximal end) of the elastic element or piece can directly or indirectly engage a portion of the pressing shaft or needle base or seat. The elastic element or piece can fixedly or removably engage a proximal portion of the needle base or seat. In some embodiments, the elastic element or piece is directly or indirectly coupled to the piston rod. For example, a portion (e.g., a distal end) of the elastic element or piece can directly or indirectly engage a portion (e.g., a proximal end) of the piston rod. In some embodiments, the elastic element or piece is fixedly or removably coupled to the piston rod. In some embodiments, the pressing shaft can be pushed distally relative to the housing in order to exert a force on the elastic element or piece (e.g., spring), which in turn exerts a force on the piston rod, while the syringe needle is advanced distally by the pressing shaft.

In some embodiments, the needle base or seat or a portion thereof is elongated axially, providing space between a portion of the pressing shaft and the piston rod configured to accommodate one or more elastic elements or pieces. In embodiments where multiple elastic elements or pieces are used, any two or more of the elastic elements or pieces can be arranged in tandem or in parallel. Each elastic element or piece can be in the form of a flexible sheath or tube, a spring, an annular ring, an elongated rod or stripe, or any combination thereof. The elastic element or piece can be arranged in parallel with the needle base or seat, and/or allow the needle base or seat to pass through. For example, an elongated needle base or seat can pass through the coils of a spring, where a proximal end of the spring engages a proximal portion of the elongated needle base or seat, and a distal end of the spring engages a proximal portion of the piston rod. A distal portion of the elongated needle base or seat may be inserted in an internal lumen of the piston rod, and all or a portion of the syringe needle can be housed in the internal lumen of the piston rod. In some embodiments, prior to medical penetration using the syringe needle, the syringe needle is positioned in the internal lumen without pass through the distal end of the piston rod or the a seal (e.g., plunger seal 3 in FIG. 12) attached thereto. As such, in some embodiments, the pressing shaft (e.g., comprising or connected to elongated needle base or seat) can be configured to elastically engage the piston rod (e.g., via spring 5 in FIG. 12), a distal portion of the piston rod engaging a seal such that the seal can be configured as a floating seal.

In some embodiments, the piston rod (e.g., push rod 15 in FIG. 12) is configured to receive and/or house the syringe needle (e.g., syringe needle 6 in FIG. 12) or at least a portion thereof. In some embodiments, the piston rod is hollow. In some embodiments, the piston rod comprises an internal lumen configured to receive and/or house the syringe needle or at least a portion thereof. The internal lumen of the piston rod may but does not need to be configured to receive and/or house a flowable composition (e.g., a drug composition). In some embodiments, the internal lumen of the piston rod contains a gas (e.g., air) and houses the syringe needle but does not contain a liquid such as a drug solution. In some embodiments, the piston rod can be used to draw a flowable composition. In some embodiments, the piston rod can be pulled by a handle (e.g., handle 21 in FIG. 12) to draw the flowable composition into a syringe (e.g., syringe 1 in FIG. 12). In some embodiments, the piston rod can be used to inject a flowable composition. In some embodiments, the piston rod can be pushed by the pressing shaft (e.g., via spring 5 in FIG. 12), and the syringe needle inside the piston rod can pass through a seal (e.g., plunger seal 3 in FIG. 12) at the distal end of the piston rod. In some embodiments, there is a needle body opening between the proximal end and the distal end of the syringe needle, and the flowable composition in the syringe can contact the needle body opening once the needle body opening is distal to the seal. In some embodiments, a needle body passageway connects the needle body opening to a needle distal opening, such that a pressure different between the needle body opening (e.g., when it is inside the syringe and contacting the flowable composition) and the needle distal opening can drive the flowable composition through the needle body passageway, thereby injecting the flowable composition (through the needle distal opening) into an apparent or potential tissue void, cavity, or vessel.

In some embodiments, a portion of the piston rod (e.g., push rod 15 in FIG. 12) is configured to engage a guide tube (e.g., guide tube 16 in FIG. 12). In some embodiments, the guide tube is a tube provided inside the housing. In some embodiments, the guide tube is provided inside a another tube within the housing. In some embodiments, a portion of the piston rod slidably engages an inner surface of the guide tube, such that the piston rod can move axially relative to the guide tube. In some embodiments, a portion of the pressing shaft is configured to engage the guide tube. In some embodiments, a portion of the pressing shaft slidably engages an inner surface of the guide tube, such that the pressing shaft can move axially to move the syringe needle relative to the guide tube. In some embodiments, the guide tube may comprise a structure (e.g., one or more axial ridges or grooves) on an internal surface that slidably engage a corresponding structure (e.g., one or more axial grooves or ridges) on an outside surface of the pressing shaft and/or on the piston rod. The corresponding structures (e.g., axial ridges and grooves) can allow sliding movement of the pressing shaft and/or the piston rod in a axial direction, while maintaining positional stability and/or minimizing movement of the syringe needle in other directions (e.g., radially). In some embodiments, a proximal portion of the piston rod comprises a protrusion (e.g., one or more annular ridges) that engages an internal surface of the guide tube. As such, in some embodiments, the piston rod can be considered a floating structure in that it slidably engages an inner surface of the guide tube and can be moved axially relative to the guide tube due to the engagement of the piston rod with the spring. In some embodiments, the guide tube is fixed relative to the housing.

In some embodiments, a distal portion of the piston rod (e.g., push rod 15 in FIG. 12) is configured to engage the seal (e.g., plunger seal 3 in FIG. 12). In some embodiments, the piston rod is configured to slidably engage an internal surface of the syringe (e.g., syringe 1 in FIG. 12). In some embodiments, the seal is a floating seal that slidably and sealingly engages an internal surface of syringe. In some embodiments, the seal separates a proximal lumen and a distal lumen formed by a syringe barrel of the syringe, where the distal lumen of the syringe is configured to draw and/or store a flowable composition. In some embodiments, the seal together with a syringe barrel of the syringe forms a lumen that is configured to draw and/or store a flowable composition. In some embodiments, the seal is on the distal end of the piston rod inserted in the syringe.

In some embodiments, the syringe (e.g., syringe 1 in FIG. 12) is configured to engage the housing. In some embodiments, a proximal portion of the syringe fixedly or removably engages the housing. In some embodiments, a distal portion of the syringe fixedly or removably engages the distal seal (e.g., sealing tip 8 in FIG. 12). In some embodiments, an internal lumen of the syringe is configured to draw and/or store a flowable composition such as a drug composition. In some embodiments, the internal lumen configured to contain the flowable composition is distal to the floating seal (e.g., plunger seal) and proximal to the distal seal (or sealing tip), and is formed by sealing engagement between the syringe and the floating seal and between the syringe and the distal seal. In some embodiments, the distal seal sealingly engages the distal end of the syringe. In some examples, the distal seal can be pressed onto the distal end of the syringe in order to form the sealing engagement. Exemplary configurations of the distal seal are shown in FIGS. 16A-16C and the distal seal can have a flat distal portion, a spherical distal portion, or a cone-shaped distal portion. The distal seal can have a distal portion having a flat distal surface, a convex surface, a spherical surface, a concave surface, or a distal surface of any other suitable shape.

In some examples, the distal seal can comprise a proximal portion that inserts into the syringe to form a sealing engagement with an internal surface of the syringe. In some examples, the portion of the distal seal and the internal surface of the syringe can comprise corresponding structures (e.g., protrusions such as threads and ridges, e.g., an annular ridge, and indentations such as grooves, e.g., annular groove) that engage each other. For instance, the portion of the distal seal can comprise a thread on an outside surface that engages a thread on internal surface of a distal portion of the syringe. In some examples, the distal seal can comprise a portion that engages an outside surface of the syringe. In some examples, the portion of the distal seal and the outside surface of the syringe can comprise corresponding structures (e.g., protrusions such as threads and ridges, and indentations such as grooves) that engage each other. For instance, the portion of the distal seal can comprise a thread on an internal surface that engages a thread on an external surface of a distal portion of the syringe.

In some examples, the distal seal can comprise a proximal portion that engages a gland (e.g., gland 23 shown in FIG. 12). In some examples, an internal surface of the gland and an outside surface of the syringe can comprise corresponding structures (e.g., protrusions such as threads and ridges, e.g., an annular ridge, and indentations such as grooves, e.g., annular groove) that engage each other, e.g., via threaded engagement. In some examples, the gland engages the distal seal at an annular groove 24 and presses the distal seal against the distal opening of the syringe barrel to form a sealing engagement.

In some embodiments, a device disclosed herein comprises a stopper, e.g., limiter 18 in FIG. 12. In some embodiments, the stopper can be used to limit the maximal length of an axial movement of the pressing shaft, e.g., in order to achieve precise injection. In some embodiments, the stopper can be used to limit a rotation and/or a radial movement of the pressing shaft, e.g., in order to prevent or minimize deviation of the pressing shaft (and the needle base and syringe needle coupled thereto) from a central axis of the assembled device. In some embodiments, the stopper can engage the guide tube. In some embodiments, the stopper can engage the fixedly or removably engage the proximal end of the guide tube. In some embodiments, the guide tube can be used to guide the movement of the pressing shaft and the piston rod, e.g., through corresponding structures on the components, in order to achieve precision of the axial movement of the pressing shaft and the piston rod, as well as precision of the syringe needle movement. In some embodiments, the device through a combination of features (e.g., the stopper and the guide tube)

prevents or minimizes the rotation and/or deviation (e.g., from a central axis) of the pressing shaft, the piston rod, the needle base or seat, and/or the syringe needle, both during transportation and storage of the assemble device and during the use of the device for medical penetration.

In some embodiments, a device disclosed herein comprises a ruler, e.g., ruler 19 in FIG. 12. In some embodiments, the ruler can be used to measure or otherwise determine a distance between a penetration site (e.g., a site to be penetrated by the syringe needle) and the corneal limbus, which is the border between the cornea and the sclera. In some embodiments, the distal end of the ruler can be configured to contact a portion of the eye at the injection site. In some embodiments, the protrusion of the ruler can be configured to leave a marker on a portion of the eye, for example, at the injection site. For example, the marker can indicate the injection site. For example, the marker may appear as parallel marker lines on the conjunctiva of the eye, indicating to the user that injection should be performed in the area between the parallel marker lines. In some embodiments, the ruler may be removably coupled to the delivery device, for example, at the distal end (e.g., coupled to the distal seal 8 in FIG. 12 or coupled to the contacting element 1b in FIG. 1A) of the delivery device. In such embodiments, the ruler may be removed from the delivery device after marking the injection site on the target tissue.

In some embodiments, a device disclosed herein comprises an adapter, e.g., adapter 20 in FIG. 12. In some embodiments, the adapter can comprise a distal end comprising a plurality of distal petals and/or a proximal end comprising a plurality of proximal petals. In some embodiments, the adapter can comprise an adapter needle. In some embodiments, the adapter can be used to transfer a flowable composition from a container (e.g., a vial) to the syringe of the device disclosed herein. In some embodiments, the syringe can be inserted into the proximal end of the adapter. For instance, the distal seal (e.g., sealing tip 8 in FIG. 12) can be inserted inside the adapter, where the adapter needle contacts and passes through the distal seal to establish a fluid communication with an internal lumen of the syringe, where the internal lumen of the syringe is distal to the floating seal. The fluid communication can allow passage of a gas, a liquid, or a mixture thereof. In some embodiment, the adapter needle can be inserted into a container (e.g., a vial) containing a flowable composition (e.g., a drug solution), e.g., by using the adapter needle to penetrate a seal of the container, thereby establishing a fluid communication between the internal lumen of the syringe and the inside of the container. In some embodiments, a handle (e.g., handle 21 in FIG. 12) configured to engage a proximal portion of the piston rod can be used to push and/or pull the piston rod in an axial direction relative to the syringe. For example, the handle can be pulled proximally to draw the flowable composition from the container into the internal lumen of the syringe via the adapter needle. In another example, the handle can be pushed distally to expel gas and/or liquid via the adapter needle. For instance, the handle can be pulled proximally to draw a liquid (e.g., a drug solution) along with undesired gas (e.g., air) into the syringe, and then the assembly comprising the syringe and the adapter can be positioned with the adapter needle pointing upwards (e.g., vertically), such that the handle can be pushed distally (e.g., in an upward direction) to expel the undesired gas through the adapter needle, leaving the flowable composition in the syringe.

In some embodiments, provided herein is a method of using a device describe herein for medical penetration. In some embodiments, a preassembled device is provided, as shown in FIG. 13A. In some embodiments, the housing of the preassembled device can be rotated to separate the syringe from the main body of the device. In some embodiments, a proximal portion of the syringe can be in threaded engagement with a distal portion of the housing. For example, the proximal portion of the syringe can comprise threaded grooves on its internal surface which are configured to engage threaded ridges on the outside surface of the distal portion of the housing, as shown in FIG. 13B.

After separation of the syringe, in some embodiments, the proximal end of the piston rod is exposed. A handle can be attached to the piston rod, e.g., via threaded engagement with the proximal end of the piston rod, as shown in FIG. 13C. In some embodiments, an adapter comprising an adapter needle enclosed therein can be attached to the syringe. In some embodiments, the adapter comprises a distal opening and a proximal opening. In some embodiments, the distal end of the syringe (e.g., with the distal seal attached thereto) is inserted into the proximal opening of the adapter, thereby contacting the adapter needle with the distal seal attached to the syringe. In some embodiments, the proximal end of the adapter needle passes through the distal seal attached to the syringe, such that a proximal opening of the adapter needle is inside the internal lumen of the syringe. In some embodiments, a container or a portion thereof containing a flowable composition (e.g., a drug composition) is inserted into the distal opening of the adapter, thereby contacting the adapter needle with the container. In some embodiments, the distal end of the adapter needle inserts into the container, such that a distal opening of the adapter needle is inside the container and capable of establishing a fluid communication between the flowable composition and the internal lumen of the syringe. In some embodiments, the handle is pulled to move the piston rod proximally and draw the flowable composition into the internal lumen of the syringe through the adapter needle, and undesired gas can be expelled by pushing the handle to move the piston rod distally. By pulling and/or pushing the handle, the seal at the distal end of the piston rod and inside the syringe can be placed at a position to set a suitable volume of the flowable composition in the syringe, for example, 0.1 mL or 0.05 mL, as shown in FIG. 13D, and the handle and the adaptor can then be disconnected from the piston rod and the syringe, respectively. The syringe with the flowable composition inside can be connected with the body of the device, e.g., by inserting the syringe needle (e.g., 6 as shown in FIG. 13B) into the piston rod (e.g., 15 as shown in FIG. 13D), inserting the piston rod into the guide tube inside the housing, and screwing the proximal end of the syringe back onto the distal end of the housing, as shown in FIG. 13E.

After the assembly, the pressing shaft can be pushed in the distal direction to a position. In some embodiments, the position is a predetermined position. In some embodiments, the position can be adjusted as needed. In some embodiments, the pressing shaft is pushed to the position such that the elastic element or piece (e.g., a spring) becomes compressed. In some embodiments, the sealing tip can be contacted with an eye, e.g., an area in the sclera of the eye, and kept stable. In some embodiments, the control knob can be rotated to advance the pressing shaft in a distal direction, thereby advancing the syringe needle attached to the pressing shaft distally toward and/or through the seal inside the syringe. The seal can be a floating seal and the syringe needle can pass through the seal by piercing the seal or inserting through a pre-existing aperture in the seal. The syringe needle can be further advanced to pass through the sealing tip, as shown in FIG. 13F, and to pierce into the sclera of the eye. In some embodiments, since the sclera is a dense tissue, the pressure at the distal opening of the syringe needle is greater than the pressure at the body opening of the syringe needle, which can be in fluid communication with the flowable composition inside the syringe; under such conditions, the syringe needle may be further advanced in the sclera without changing the position of the floating seal inside the syringe. In some embodiments, the position of the floating seal inside the syringe is monitored as an operator pushes the pressing shaft to advance the syringe needle. Once the distal opening of the syringe needle is outside the sclera and into the choroid/ciliary body, the pressure at the distal opening of the syringe needle decreases, and the pressure at the body opening of the syringe needle can drive the flowable composition through the needle body passageway and discharge it from the syringe needle distal opening, thereby creating and expanding a suprachoroidal space containing the flowable composition, which may comprise a liquid, a solution, a suspension, a gel, an oil, an ointment, an emulsion, a cream, a foam, a lotion, and/or a paste. Since a portion of the flowable composition inside the syringe is discharge, the seal (along with the piston rod) is moved to a more distal position in the syringe. Thus, by observing the movement of the seal, an operator can determine whether the distal opening of the syringe needle has exited a first tissue and reached a second, less dense tissue, e.g., from the sclera into the choroid/ciliary body. In some embodiments, as soon as the seal moves and passes a preset mark or indicator line for volume (e.g., 0.1 mL or 0.05 mL), the distal advancement of the syringe needle (e.g., via scrolling or pressing the control knob) is stopped. In some embodiments, the position of the syringe needle is the tissue is maintained for a period of time, e.g., Is, 2 s, 3 s, 4 s, 5 s, 6 s, 7 s, 8 s, 9 s, 10 s, or more, to allow the spring to act on the piston rod, thereby releasing the tension in the spring and moving the seal distally. In some embodiments, the tension force in the spring is sufficient to push the piston rod and the seal attached thereto (e.g., without moving the position of the syringe needle inside the tissue) to a predetermined, more distal position inside the syringe (e.g., the distal end of the lumen of the syringe), thereby injecting a predetermined volume of the flowable composition into the tissue (e.g., into the suprachoroidal space). In some embodiments, the predetermined volume is about 0.05 mL, 0.075 mL, about 0.1 mL, about 0.125 mL, about 0.15 mL, about 0.175 mL, about 0.2 mL, or more. In some embodiments, the predetermined volume is set when the flowable composition is drawn into the syringe, for example, using a handle and an adapter as shown in FIG. 13D. After injection, the syringe needle can be removed from the tissue.

In some examples, for instance as shown in FIGS. 13A-13F, the syringe is not prefilled with a flowable material or composition, and the flowable material or composition is drawn from a container into the syringe prior to delivery into a tissue or apparent or potential tissue void, cavity, or vessel.

In some examples, for instance as shown in FIGS. 17A-17B, the syringe of a device disclosed herein can be prefilled with a flowable material or composition. In some embodiments, the syringe (e.g., syringe 1 show in FIG. 12) can be provided in one or more parts. In some embodiments, a container (e.g., a syringe unit), e.g., as shown in FIGS. 17A-17B, can comprise a cylindrical wall sealingly engaging a fixed seal (which can be fixed to the container at a distal end of the container and can be passed through by the needle) and a floating seal (which can move inside the container and can be passed through by the needle), and the space enclosed by the cylindrical wall, the fixed seal and the floating seal can be prefilled with a flowable material or composition. In some embodiments, the device or system can comprise a first syringe unit and the container can be a second syringe unit configured to engage the distal end of the first syringe unit. The container (e.g., syringe unit) can be inserted into or attached to the body (e.g., to the first syringe unit) of the device prior to or after the flowable material or composition is filled into the container (e.g., syringe unit). In some embodiments, the floating seal in the container (e.g., syringe unit) may contact the distal end of the piston rod, thereby establishing an engagement between the piston rod and the floating seal that transmits a force from the spring to the floating seal. The fixed seal at the distal end of the container (e.g., syringe unit) may contact a contacting element at the distal end of the device, and the contacting element can be a distal seal of the syringe as shown in FIG. 17A. In some embodiments, the fixed seal of the container (e.g., syringe unit) also serves as a distal seal of the syringe and/or as a contacting element, e.g., as shown in FIG. 17B. In some embodiments, the container (e.g., syringe unit) can be configured to at least partially insert into a syringe barrel, for instance, as shown in FIGS. 17A-17B. In some embodiments, the fixed seal sealingly engages the container (e.g., syringe unit) which in turn engages an inside wall of the syringe barrel. In some embodiments, the fixed seal sealingly engages both the container (e.g., syringe unit) and an inside wall of the syringe barrel. The engagement between the container (e.g., syringe unit) and the syringe barrel and the engagement between the fixed seal and a wall of the container can comprise any suitable engagement, such as via insertion, a threaded engagement, a non-threaded engagement, engagement secured by a clip, engagement secured by a gland, or any combination thereof.

In some embodiments, a device disclosed herein achieves precise control of the syringe needle as it advances through one or more tissues, and is particular useful for accessing an apparent or potential tissue void, cavity, or vessel, such as potential space between two adjacent tissues having different densities. In some embodiments, a device disclosed herein achieves precise access of a suprachoroidal space, while reducing or minimizing the risk of insufficient penetration and/or the risk of overshooting, e.g., the needle going too deep into the choroid/ciliary body and/or damaging the retina. In some examples, the axial movement of the syringe needle can be controlled and reach micron precision as it advances in the tissue. In some examples, the axial movement of the syringe needle in the tissue can be set to be within any distance that meets the requirement of the tip of the syringe needle penetrating from a surface of an eye into a suprachoroidal space of the eye. In some examples, the axial movement distance of the syringe needle in the tissue can be set to be within a length of between about 0 and about 4.0 mm, e.g., between about 0 and about 0.5 mm, between about 0 and about 1.0 mm, between about 0 and about 1.5 mm, between about 0 and about 2.0 mm, or between about 0 and about 2.5 mm. In some embodiments, a device disclosed herein comprises a syringe needle (e.g., 6 as shown in FIG. 12) of a size and configuration disclosed herein, e.g., the syringe needle having a bevel angle between about 0 degree and about 40 degrees, particularly between about 5 degrees and about 30 degrees, such as between about 15 degree and about 25 degrees. In some embodiments, the volume of the flowable composition to be delivered (e.g., via injection) using a device disclosed herein can be selected based on the conditions of a particular subject, and can be adjusted according to changes in the conditions. In some embodiments, the energy stored in the energy storage member (e.g., spring) is automatically released to advance the floating seal (e.g., via a piston rod 15 in FIG. 12), thereby discharging a volume of the flowable composition into an apparent or potential tissue void, cavity, or vessel. Given the combination of various features disclosed herein, the devices and methods disclosed herein can achieve precise, safe, and controllable delivery of agents into a tissue of a subject, such as the suprachoroidal space, or other apparent or potential tissue void, cavity, or vessel.

In some embodiments, disclosed herein in a device or system for subretinal delivery of a substance (e.g., a drug substance) based on accessing the suprachoroidal space and/or delivering a composition between the sclera and the choroid/ciliary body of an eye. In some embodiments, a device or system disclosed herein comprises a cannula (e.g., a microcannula), a microneedle, and an operation module (e.g., comprising a handle or knob configured to control the advancement or retraction of the microneedle and the advancement or retraction of the flexible cannula). In some embodiments, the cannula comprises a distal tip which may comprise a sharp tip, a stylet, a bevel, or a blunt tip. In some embodiments, the cannula comprises a flexible body. In some embodiments, the cannula is configured to be inserted into the bleb or bulge in the suprachoroidal space, through the passageway created by the syringe needle used for injection of a viscoelastic composition into the suprachoroidal space. In some embodiments, the operation module is configured to control cannula placement and delivery to achieve minimally invasive operation. In some embodiments, the microneedle has a curved tip and is configured to be housed in the cannula. In some embodiments, the microneedle is configured to be advanced and/or retracted through an internal lumen of the cannula. After the cannula is advanced between a choroid/ciliary body and a sclera of a patient's eye to a location in the posterior segment, a distal tip of the microneedle can be exposed, e.g., by advancing the microneedle through the cannula. In some embodiments, since the microneedle has a curved distal tip, the distal tip can pierce the choroid/ciliary body at a certain angle to achieve delivery of a composition under the retina without removing the vitreous or creating a retinotomy (e.g., by piercing the retina). In some embodiments, a proximal end of the cannula is configured to be engage a distal connector of the operation module. In some embodiments, the operation module comprises one or more elements configured to engage the microneedle in order to control movement of the microneedle inside an internal lumen of the cannula. In some embodiments, a distal connector of the operation module is configured to engage one or more syringes through one or more adapters. In some embodiments, each syringe is connected to an adapter that is connected to the operation module. In some embodiments, the one or more syringes can contain one or more compositions, such as a flowable material, a viscoelastic material, or an infusate, and delivery of the composition(s) through the microneedle can be controlled.

In some embodiments, a flowable composition such as an viscoelastic composition can be injected via the syringe needle of an injection device disclosed herein into an eye between the sclera and the choroid/ciliary body, thereby forming a suprachoroidal space containing the flowable composition. In some embodiments, the viscoelastic material forms a bleb or bulge between the sclera and the choroid/ciliary body. In some embodiments, the distal tip of a linear member such as a flexible cannula can be placed in the bleb. In some embodiments, the distal tip of the linear member is advanced through an internal lumen of the syringe needle such that it can placed in the bleb and further advanced between the sclera and the choroid/ciliary body (e.g., to reach the back of the eye). In some embodiments, the distal tip of the linear member is inserted through the penetration site of the syringe needle, and advanced towards the bleb along the path created by the syringe needle. The linear member can be inserted through the path created by the syringe needle while the syringe needle remains in the eye. In some embodiments, the linear member parallels the syringe needle, and the two are next to each other in the path created by the syringe needle. In some embodiments, the linear member is inside a lumen of the syringe needle. In some embodiments, the syringe needle is inside a lumen of the linear member.

In some embodiments, the linear member such as a cannula is a thin, flexible hollow tube with a smooth round tip on the distal end, where the opposite, proximal end can have a hub (e.g., a plastic hub) that can be attached to a syringe. In some embodiments, the cannula comprises a sharp distal tip. In some embodiments, the cannula comprises a blunt distal tip. In some embodiments, the distal end of the cannula opens up a path between structures in tissue, thereby helping dissecting the structures while reducing tissue damage. In some embodiments, the cannula can comprise an opening at its distal end, e.g., at a blunt-tip of the cannula. In some embodiments, the cannula can comprise a side opening on a side wall of the cannula, whereas the distal end may or may not comprise an opening.

In some embodiments, the distal tip of the linear member (e.g., a flexible cannula) in the bleb of the flowable composition can be further advanced inside the eye, e.g., between the sclera and the choroid/ciliary body, thereby enlarging the suprachoroidal space towards the back of the eye. In some embodiments, the linear member is configured to contour to the globe of the eye and access the back of the eye, targeting a subretinal location in the posterior segment. In some embodiments, the flowable composition such as an viscoelastic composition provides lubrication of the distal tip of the linear member such that it can slide along the boundary between the sclera and the choroid/ciliary body, reducing the resistance during cannulation and/or reducing the risk of choroidal perforation or inadvertent retinal damage caused by the linear member. In some embodiments, the viscoelastic composition forms a protective layer around the distal tip of the linear member, and the protective layer can provide lubrication and guide the direction of cannulation.

In some embodiments, after the distal end of the linear member reaches a target location, e.g., at a subretinal location in the posterior segment, a composition such as an infusate can be delivered at the target location. The composition such as infusate can be delivered through one or more openings in the linear member. In some embodiments, once at a target location, a microneedle in the one or more openings of the linear member can penetrate the choroid/ciliary body. In some embodiments, as the needle tip of the microneedle pushes against the choroid/ciliary body, tissue tenting becomes visible, and advancing of the microneedle through the flexible cannula is stopped. In some embodiments, the composition such as infusate can be delivered (e.g., by applying pressure to a syringe connected to the microneedle and containing the infusate) into a subretinal space without penetrating the retina. In some embodiments, the composition such as infusate can form an entry bleb in the subretinal space. In some embodiments, the entry bleb in the subretinal space is observed and the size of the bleb is monitored. In some embodiments, after the bleb reaches a certain size, the microneedle and/or the flexible cannula can be retracted.

In some embodiments, a device or system for delivering a therapeutic agent to an eye is disclosed. In some embodiments, the device or system comprises a control module and a cannula extending distally from the control module, wherein the cannula is sized and configured to be insertable between a choroid/ciliary body and a sclera of a patient's eye, wherein the cannula defines a longitudinal axis. In some embodiments, the device or system comprises a hollow needle comprising a proximal end, wherein the needle is slidable relative to the cannula. In some embodiments, the device or system comprises an actuation member coupled to the proximal end of the hollow needle to translate the hollow needle. In some embodiments, the hollow needle is configured to translate relative to the cannula to thereby drive a distal portion of the needle along an exit axis that is obliquely oriented relative to the longitudinal axis of the cannula.

In some embodiments, the device or system comprises a fluid source in fluid communication with the proximal end of the hollow needle. In some embodiments, the needle includes a sharp distal tip. In some embodiments, the sharp distal tip of the needle comprises a first bevel, a second bevel, and optionally a third bevel, wherein the first bevel, second bevel, and optional third bevel are each oriented obliquely relative to each other. In some embodiments, the exit axis is oriented at an angle between approximately 5° and approximately 30° relative to the longitudinal axis of the cannula. In some embodiments, the exit axis is oriented at an angle between approximately 7° and approximately 9° relative to the longitudinal axis of the cannula. In some embodiments, the cannula includes a beveled distal end, wherein the beveled distal end has a bevel angle, wherein the bevel angle is between approximately 10° and approximately 30°. In some embodiments, the cannula defines a plurality of lumens extending longitudinally through the length of the cannula, wherein at least one lumen of the plurality of lumens is configured to slidably receive the needle. In some embodiments, the cannula has a flexural stiffness between $0.5 \times 10^{-6}$ Nm$^2$ and $12 \times 10^{-6}$ Nm$^2$. In some embodiments, the cannula has a flexural stiffness between $2.0 \times 10^{-6}$ Nm$^2$ and $8.0 \times 10^{-6}$ Nm$^2$. In some embodiments, the cannula has a bending stiffness of about $1.0 \times 10^{-6}$, about $1.5 \times 10^{-6}$, about $2.0 \times 10^{-6}$, about $2.2 \times 10^{-6}$, about $2.4 \times 10^{-6}$, about $2.6 \times 10^{-6}$, about $2.8 \times 10^{-6}$, about $3.0 \times 10^{-6}$, about $3.2 \times 10^{-6}$, about $3.4 \times 10^{-6}$, about $3.6 \times 10^{-6}$, about $3.8 \times 10^{-6}$, about $4.0 \times 10^{-6}$, about $4.2 \times 10^{-6}$, about $4.4 \times 10^{-6}$, about $4.6 \times 10^{-6}$, about $4.8 \times 10^{-6}$, about $5.0 \times 10^{-6}$, about $5.2 \times 10^{-6}$, about $5.4 \times 10^{-6}$, about $5.6 \times 10^{-6}$, about $5.8 \times 10^{-6}$, about $6.0 \times 10^{-6}$, about $6.2 \times 10^{-6}$, about $6.4 \times 10^{-6}$, about $6.6 \times 10^{-6}$, about $6.8 \times 10^{-6}$, about $7.0 \times 10^{-6}$, about $7.2 \times 10^{-6}$, about $7.4 \times 10^{-6}$, about $7.6 \times 10^{-6}$, about $7.8 \times 10^{-6}$, about $8.0 \times 10^{-6}$, about $8.5 \times 10^{-6}$, about $9.0 \times 10^{-6}$, about $9.5 \times 10^{-6}$, about $10.0 \times 10^{-6}$, about $10.5 \times 10^{-6}$, about $11.0 \times 10^{-6}$, or about $11.5 \times 10^{-6}$ Nm$^2$.

In some embodiments, provided herein is a method for use of a device or system comprising a cannula and a hollow needle that is movable relative to the cannula. In some embodiments, the method comprises forming an incision in an eye of a patient and inserting the cannula through the incision, wherein the incision extends through a sclera layer of the eye to provide access to a suprachoroidal space of the eye. In some embodiments, the incision can be formed by the syringe needle of a device or system disclosed herein, e.g., syringe needle 6 in FIGS. 1A-1E through FIGS. 11A-11B or syringe needle 6 in FIG. 12 and FIGS. 13A-13F.

In some embodiments, the method comprises incising at least a portion of the eye to provide access to the choroid/ciliary body of the eye. In some embodiments, the method comprises guiding a cannula into an incision created by incising at least a portion of the eye. In some embodiments, the method comprises advancing the cannula between the choroid/ciliary body and the sclera to position the distal end of the cannula at a posterior region of the suprachoroidal space. In some embodiments, at least a portion of the inserted cannula is flexible and conforms to a curvature of the eye during positioning of the distal portion of the inserted cannula, for example, by advancing the cannula tangentially along at least one of the choroid/ciliary body layer of the eye or the sclera layer of the eye within a space between the choroid/ciliary body layer of the eye and the sclera layer of the eye. In some embodiments, the method comprises guiding the cannula to an injection site (e.g., in the posterior segment) by direct visualization through the pupil of the eye.

In some embodiments, the method comprises advancing a needle through the cannula to penetrate through the choroid/ciliary body. In some embodiments, the method comprises advancing the needle relative to the cannula and through the choroid/ciliary body and into a subretial space, without perforating the retina. In some embodiments, the needle is advanced from the distal portion of the flexible cannula along a path that is transverse to a longitudinal axis defined by the flexible cannula, such that a distal end of the needle pierces the choroid/ciliary body layer of the eye. In some embodiments, the method comprises delivering a composition, e.g., a composition comprising a therapeutic agent into the subretinal space via the advanced needle. In some embodiments, the method comprises delivering a leading bleb of fluid via the advanced needle before delivering the composition comprising the therapeutic agent via the advanced needle.

For instance, as shown in FIG. 18, disclosed herein is a method of delivering a flowable composition into an eye of a subject using a device or system disclosed herein. In some embodiments, the syringe needle is inserted into the eye and the needle distal opening is placed at a position between the sclera and the choroid/ciliary body of the eye. In some embodiments, the flowable composition enters the needle body opening, is passed through the body passageway (e.g., due to a force applied to the piston rod 15 and the floating seal 3 by the spring 5, shown in FIG. 12), and is discharged from the needle distal opening into a suprachoroidal space (SCS) in the eye. A viscoelastic material can be injected between the sclera and the choroid/ciliary body to form the SCS, as shown in FIG. 18, and the viscoelastic material can facilitate further dissection of the choroid/ciliary body from the sclera, further expanding the SCS. The viscoelastic material can also lubricate a flexible cannula inserted into the SCS and help navigate a distal tip of the cannula between the sclera and the choroid/ciliary body towards to the back of the eye, while minimizing the risk of the cannula tip piercing through the choroid/ciliary body and into the retina. Thus, as shown in FIG. 18, in some embodiments, once the SCS is formed, the syringe needle can be removed, leaving the injection site and the SCS filled with the viscoelastic material. The injection site may but does not need to be expanded, for instance, by creating a larger incision from the injection site. In some embodiments, as shown in FIG. 18, a cannula is inserted through the injection site into the suprachoroidal space and advanced towards a posterior segment of the eye. The cannula may contain a microneedle which can be advanced and/or exposed such that a distal end of the microneedle pierces the choroid/ciliary body without piercing the retina. In some embodiments, as shown in FIG. 18, a composition can be delivered into a subretinal space through the microneedle without removing the vitreous or passing a needle through the vitreous and the retina.

The exemplary embodiments and optional implementations of the present disclosure are described in detail above in combination with the figures. However, the present disclosure is not limited to the details described in the embodiments described above. Simple variants can be applied to the embodiments of the present disclosure, all of which are within the scope of the present disclosure.

It should be noted that, each of the technical features described in the embodiments above, when not in conflict, can be combined in any reasonable manner. To avoid unnecessary repetition, the possible combinations are not described separately in the embodiments.

Additionally, the different implementations of the embodiments of the present disclosure can be freely combined. As long as they do not go against the ideas of the present disclosure, they should also be considered part of this disclosure.

The invention claimed is:

1. A device, comprising:
a syringe barrel comprising a proximal open end and a distal closed end;
an actuation unit in the syringe barrel, wherein the actuation unit comprises a needle base, a floating seal, and an energy storage member between the needle base and the floating seal, and wherein the needle base is proximal to the floating seal;
a needle comprising a needle proximal end engaging the needle base and a needle distal end, wherein the needle comprises:
(i) a needle distal opening,
(ii) a needle body opening between the needle proximal end and the needle distal end, wherein the needle body opening is proximal to the needle distal opening, and
(iii) a needle body passageway connecting the needle distal opening and the needle body opening; and
a flowable composition lumen distal to the floating seal, wherein the actuation unit is configured to advance the needle to place the needle proximal end and/or the needle distal end in the flowable composition lumen.

2. The device of claim 1, wherein the flowable composition lumen comprises a flowable composition selected from the group consisting of a liquid, a solution, a suspension, a gel, an oil, an ointment, an emulsion, a cream, a foam, a lotion, a paste, and any combination thereof.

3. The device of claim 1, wherein the flowable composition lumen does not comprise a gas.

4. The device of claim 1, wherein the syringe barrel does not contain a flowable composition between the floating seal and the needle base, wherein the flowable composition is selected from the group consisting of: a liquid, a solution, a suspension, a gel, an oil, an ointment, an emulsion, a cream, a foam, a lotion, a paste, and any combination thereof.

5. The device of claim 1, wherein the syringe barrel is filled with a gas between the floating seal and the needle base.

6. The device of claim 1, wherein the needle base engages an actuation member on the proximal open end of the syringe barrel, wherein the actuation member is configured to advance the needle base and the needle distally.

7. The device of claim 1,
wherein the energy storage member is a first energy storage member, the actuation unit further comprises a second energy storage member elastically engaging a slider and the floating seal, and a portion of the slider extends outside the syringe barrel.

8. The device of claim 7, wherein the energy storage member comprises a spring and/or an elastic sheath.

9. The device of claim 7, wherein the energy storage member is releasably connected to the needle base and/or the floating seal.

10. The device of claim 7, wherein the energy storage member is configured to exert a force on the floating seal which in turn exerts a force on a flowable composition in the flowable composition lumen.

11. The device of claim 1, comprising a sheath configured to enclose all or a portion of the needle.

12. The device of claim 1, comprising a stopper in the flowable composition lumen, wherein the stopper is configured to stop the floating seal from moving distally.

13. The device of claim 1, comprising a distal seal at the distal closed end of the syringe barrel.

14. The device of claim 1, comprising a contacting element at the distal closed end of the syringe barrel.

15. The device of claim 1, comprising a guiding structure configured to guide a linear member toward, into and/or through the needle.

16. The device of claim 15, wherein the guiding structure comprises an angled guiding groove on the floating seal and the angled guiding groove extends from a proximal surface of the floating seal to a distal surface of the floating seal.

17. The device of claim 15, wherein the device further comprises the linear member selected from the group consisting of: a guidewire, a sheath, a catheter, a cannula, a microneedle, an electrode, and a sensor.

* * * * *